(12) United States Patent
Moehring

(10) Patent No.: US 6,196,972 B1
(45) Date of Patent: Mar. 6, 2001

(54) DOPPLER ULTRASOUND METHOD AND APPARATUS FOR MONITORING BLOOD FLOW

(75) Inventor: Mark A. Moehring, Seattle, WA (US)

(73) Assignee: Spentech, Inc., Seattle, WA (US)

( * ) Notice: Subject to any disclaimer, the term of this patent is extended or adjusted under 35 U.S.C. 154(b) by 0 days.

(21) Appl. No.: 09/190,402

(22) Filed: Nov. 11, 1998

(51) Int. Cl.[7] .................................................... A61B 8/06
(52) U.S. Cl. ............................................ 600/454; 600/441
(58) Field of Search ................................... 600/437, 440, 600/441, 454, 455; 73/626; 333/138; 342/457

(56) References Cited

U.S. PATENT DOCUMENTS

| 4,501,277 | * | 2/1985 | Hongo | 600/441 |
| 5,103,826 | * | 4/1992 | Bonnefous | 600/454 |
| 5,785,655 | * | 7/1998 | Goodsell, Jr. et al. | 600/441 |
| 5,919,139 | * | 7/1999 | Lin | 600/443 |
| 5,997,478 | * | 12/1999 | Jackson et al. | 600/437 |
| 6,045,505 | * | 4/2000 | Holley et al. | 600/441 |

OTHER PUBLICATIONS

Omoto, R. et al., "The Development of Real–Time Two–Dimensional Doppler Echocardiography and Its Clinical Significance in Acquired Valvular Diseases With Special Reference to the Evaluation of Valvular Regurgitation", Reprinted from *Japanese Heart Journal*, vol. 25, No. 3, pp. 325–340, May, 1984.

Omoto, R. et al., "Clinical Signifcance and Prospects of Real–Time Two–Dimesional Doppler Echocardiography", Color ATLAS of Real–Time Two–Dimensional Doppler Echocardiography, Chapter 1–6, pp. 1–44, Shindan–To–Chiryo Co., Ltd. Tokyo 1984.

* cited by examiner

Primary Examiner—Marvin M. Lateef
Assistant Examiner—Ali M Imam
(74) Attorney, Agent, or Firm—Dorsey & Whitney LLP

(57) ABSTRACT

A pulse Doppler ultrasound system and associated methods are described for monitoring blood flow. A graphical information display includes simultaneously displayed depth-mode and spectrogram displays. The depth-mode display indicates the various positions along the ultrasound beam axis at which blood flow is detected. These positions are indicated as one or more colored regions, with the color indicating direction of blood flow and varying in intensity as a function of detected Doppler ultrasound signal amplitude or detected blood flow velocity. The depth-mode display also includes a pointer whose position may be selected by a user. The spectrogram displayed corresponds to the location identified by the pointer. Embolus detection and characterization are also provided.

66 Claims, 13 Drawing Sheets (2 of 13 Drawing Sheet(s) Filed in Color)

Fig. 10  166, 168, 172

EMBOLUS CHARACTERIZATION SUBROUTINE

DOPPLER ULTRASOUND METHOD AND APPARATUS FOR MONITORING BLOOD FLOW

TECHNICAL FIELD

The invention relates generally to medical monitoring and diagnostic procedures and devices, and more particularly to a Doppler ultrasound method and apparatus for monitoring blood flow.

BACKGROUND OF THE INVENTION

Doppler ultrasound has been used to measure blood flow velocity for many years. The well-known Doppler shift phenomenon provides that ultrasonic signals reflected from moving targets will have a shift in frequency directly proportional to the target velocity component parallel to the direction of the ultrasound beam. The frequency shift is the same for any object moving at a given velocity, whereas the amplitude of the detected signal is a function of the acoustic reflectivity of the moving object reflecting the ultrasound. Pulse Doppler ultrasound systems commonly produce a spectrogram of the detected return signal frequency (i.e., velocity) as a function of time in a particular sample volume, with the spectrogram being used by a physician to determine blood flow characteristics of a patient.

Some Doppler ultrasound systems also have the capability to detect and characterize emboli flowing in the bloodstream. An example Doppler ultrasound system with embolus detection capability is described in U.S. Pat. No. 5,348,015, entitled "Method And Apparatus For Ultrasonically Detecting, Counting, and/or Characterizing Emboli," issued Sep. 20, 1994, to Moehring et al., the disclosure of which is incorporated herein by reference. Such ultrasound systems are advantageously used both for diagnostic exams (to determine the presence and significance of vascular disease or dysfunction) and during surgical interventions (to indicate surgical manipulations that produce emboli or alter/interrupt blood flow).

Typically, a user of ultrasound equipment finds it rather difficult to properly orient and position an ultrasound transducer or probe on the patient, as well as to select a depth along the ultrasound beam corresponding to the desired location where blood flow is to be monitored. This is particularly true in ultrasound applications such as transcranial Doppler imaging (TCD). The blood vessels most commonly observed with TCD are the middle, anterior, and posterior cerebral arteries, and the vertebral and basilar arteries. The Doppler transducer must be positioned so the ultrasound beam passes through the skull via the temporal windows for the cerebral arteries, and via the foramen magnum for the vertebral and basilar arteries. The user of the ultrasound equipment may find it difficult to locate these particular windows or to properly orient the ultrasound probe once the particular window is found.

A complicating factor in locating the ultrasound window is determination of the proper depth at which the desired blood flow is located. Commonly, the user does not know if he is looking in the correct direction at the wrong depth, the wrong direction at the right depth, or whether the ultrasound window is too poor for appreciating blood flow at all. Proper location and orientation of the Doppler ultrasound probe, and the proper setting of depth parameters, is typically by trial and error. Not only does this make the use of Doppler ultrasound equipment quite inconvenient and difficult, it also creates a risk that the desired sample volume may not be properly located, with the corresponding diagnosis then being untenable or potentially improper.

SUMMARY OF THE INVENTION

In accordance with the invention, an information display is provided in connection with Doppler ultrasound monitoring of blood flow. The information display includes two simultaneously displayed graphical displays. One graphical display is a blood locator display that indicates locations along the axis of the ultrasound beam at which blood flow is detected. The blood locator display includes a location indicator, such as a pointer directed to a selected one of the locations. The other graphical display is a spectrogram indicating velocities of monitored blood flow at the selected location. The blood locator display may include a color region corresponding with the locations at which blood flow is detected. The intensity of the color may vary as a function of detected ultrasound signal amplitude or as a function of detected blood flow velocities.

The blood locator display allows a user to quickly locate blood flow along the ultrasound beam axis. Using the blood locator display, the location of blood flow of particular interest can be further refined by the user adjusting the aim of the ultrasound probe to produce greater displayed intensity or spatial extent at the particular location of interest. The user may then select the position of the pointer to view the corresponding spectrogram. The user may also use the two simultaneously displayed graphical displays to locate a particular blood vessel by detecting temporal or other variations in the displays that are consistent with the blood vessel.

A method of detecting and characterizing an embolus is also provided. Locations in which blood does and does not flow are determined, as well as the direction of blood flow. A first ultrasound signal that may be an embolus is evaluated to determine if it corresponds with the locations where blood does and does not flow, as well as determining if it corresponds with the direction and rate of blood flow. If the first ultrasound signal does not correspond with blood flow direction or rate, then it is identified as non-embolic. If the first ultrasound signal does correspond with blood flow direction, and if it corresponds solely with locations where blood flows, then the first ultrasound signal is identified as an embolic signal of a first type. If the first ultrasound signal does correspond with blood flow direction, and if it corresponds both with locations where blood does and does not flow, then the first ultrasound signal is identified as an embolic signal of a second type.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

The following describes a novel method and apparatus for providing Doppler ultrasound information to a user, such as in connection with measuring blood velocities to detect hemodynamically significant deviations from normal values, and to assess blood flow for the occurrence of microembolic signals. Certain details are set forth to provide a sufficient understanding of the invention. However, it will be clear to one skilled in the art that the invention may be practiced without these particular details. In other instances, well-known circuits, control signals, timing protocols, and software operations have not been shown in detail in order to avoid unnecessarily obscuring the invention.

Figure 1:
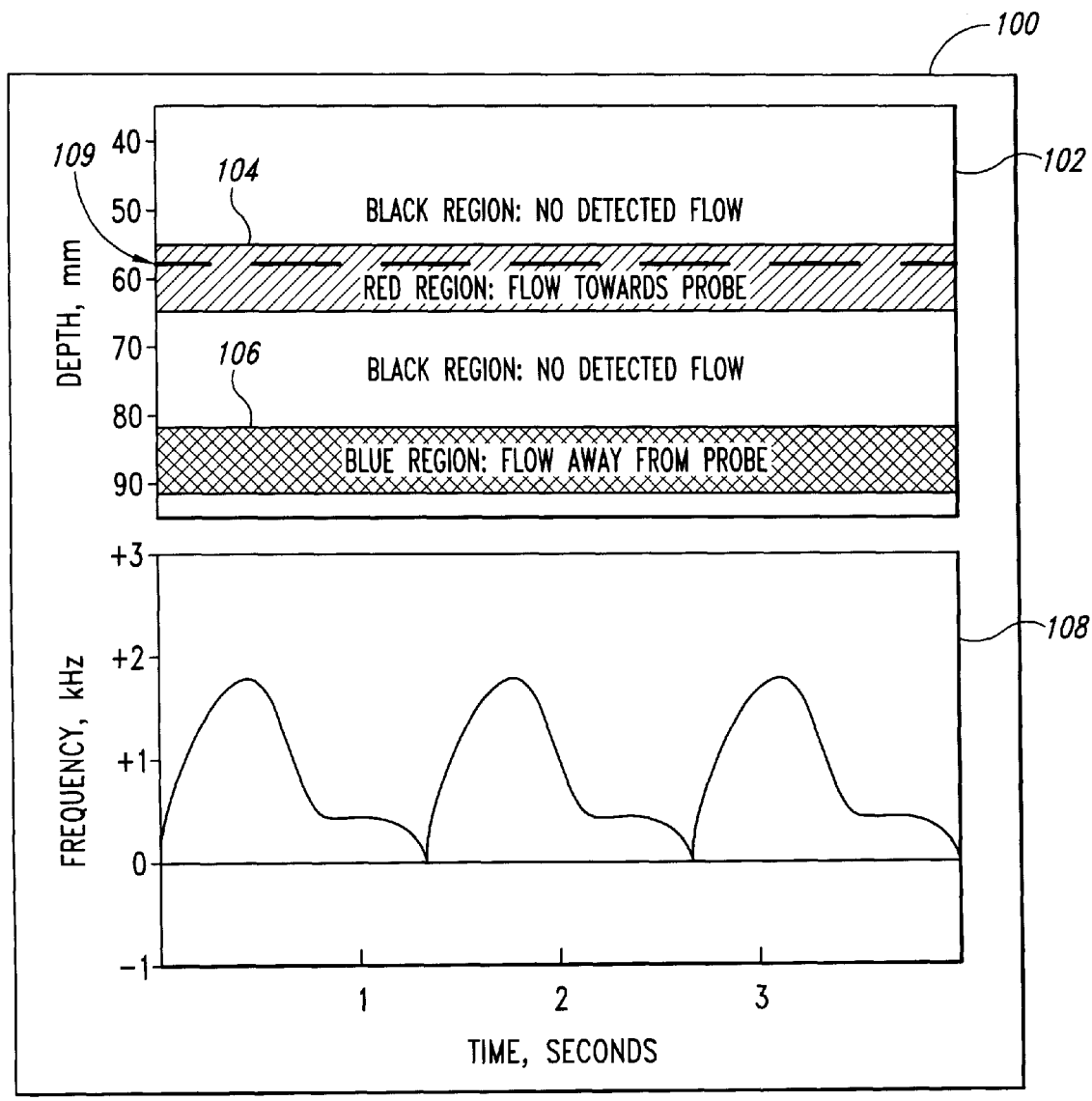
FIG. 1 is a graphical diagram depicting a first Doppler ultrasound system display mode in accordance with an embodiment of the invention.

FIG. 1 is a graphical diagram depicting a first display mode of Doppler ultrasound information in accordance with an embodiment of the invention. In this first display mode, referred to as an Aiming mode 100, two distinct ultrasound displays are provided to the user. A depth-mode display 102 depicts, with color, blood flow away from and towards the ultrasound probe at various depths along the ultrasound beam axis (vertical axis) as a function of time (horizontal axis).

The depth-mode display 102 includes colored regions 104 and 106. Region 104 is generally colored red and depicts blood flow having a velocity component directed towards the probe and in a specific depth range. Region 106 is generally colored blue and depicts blood flow having a velocity component away from the probe and in a specific depth range. The red and blue regions are not of uniform color, with the intensity of red varying as a function of the detected intensity of the return Doppler ultrasound signal. Those skilled in the art will understand that such a display is similar to the conventional color M-mode display, in which variation in red and blue coloration is associated with variation in detected blood flow velocities. However, such M-mode displays have not been used concurrently with a spectrogram and with the specific application of locating blood flow as an input to the spectrogram, from which diagnostic decisions are made.

The Aiming mode 100 also includes a displayed spectrogram 108, with FIG. 1 depicting a velocity envelope showing the characteristic systolic-diastolic pattern. Like the depth-mode display 102, the spectrogram 108 includes data points (not shown) within the velocity envelope that are colored in varying intensity as a function of the detected intensity of the return ultrasound signal. The particular sample volume for which the spectrogram 108 applies is at a depth indicated in the depth-mode display 102 by a depth indicator or pointer 109. In this way, a user of the ultrasound system can conveniently see and select particular depths at which to measure the spectrogram 108. The depth-mode display 102 readily and conveniently provides the information concerning the range of appropriate depths at which a meaningful spectrogram may be obtained.

Figure 2:
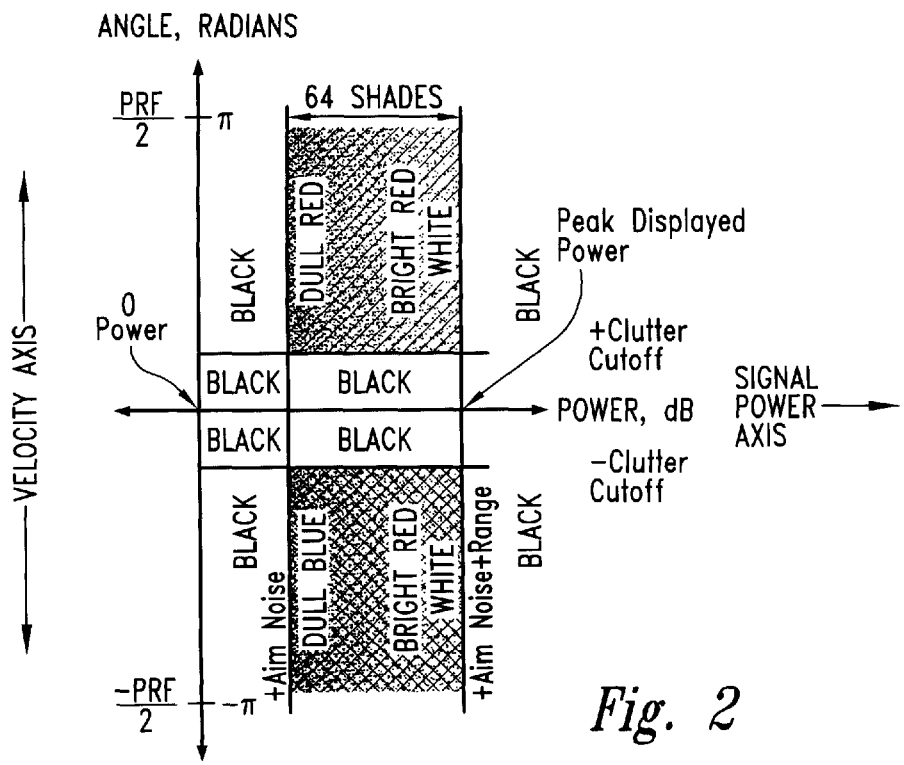
FIG. 2 is a graphical diagram depicting velocity and signal power parameters used in preparation of the display mode of FIG. 1.

As described above, the color intensity of regions 104 and 106 preferably vary as a function of the detected intensity of the return ultrasound signal. Referring to FIG. 2, a graphical diagram depicts how such color intensity is determined. In order to avoid display of spurious information, signals that may be intense but low velocity (such as due to tissue motion) are ignored and not displayed in the depth-mode display 102 of FIG. 1. This is referred to as clutter filtering and is depicted in FIG. 2 as the threshold magnitude clutter cutoff limits for positive and negative velocities. Similarly, low power signals associated with noise are also ignored and not displayed in the depth-mode display 102 of FIG. 1. The user can determine the upper power limit for the color intensity mapping by selecting a power range value. Signals above a maximum power are then ignored—another clutter filtering which is especially helpful when monitoring blood flow in the cardiac environment. Those skilled in the art will appreciate that other filtering techniques may be employed to improve the depth-mode display image, including delta modulator or other suitably adapted filtering techniques.

Figure 3:
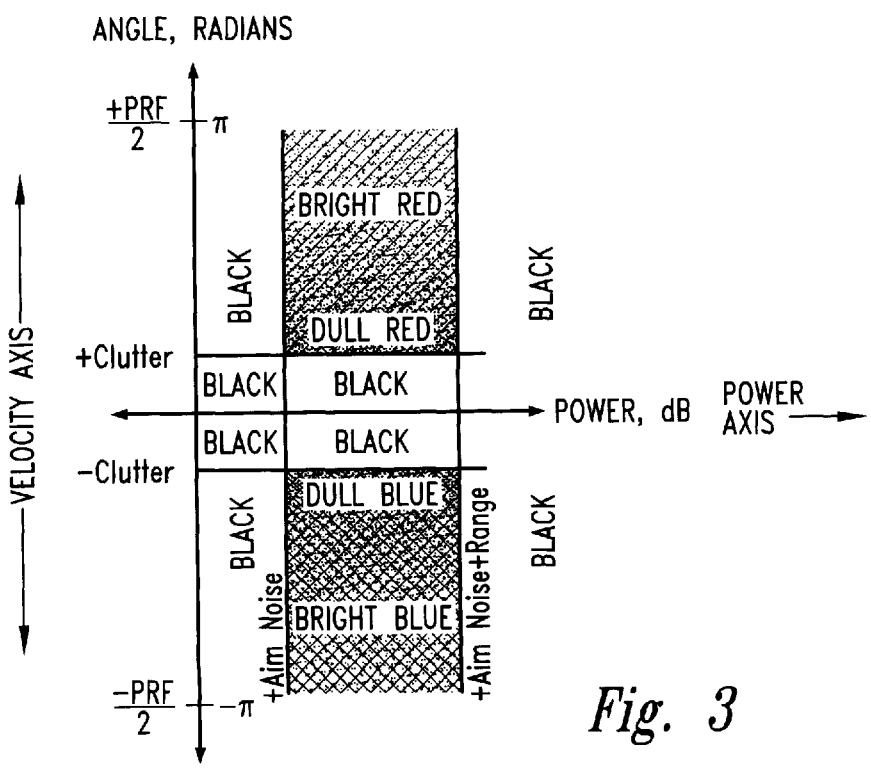
FIG. 3 is a graphical diagram depicting velocity and signal power parameters used in preparation of an alternative embodiment of the display mode of FIG. 1.
Figure 4:
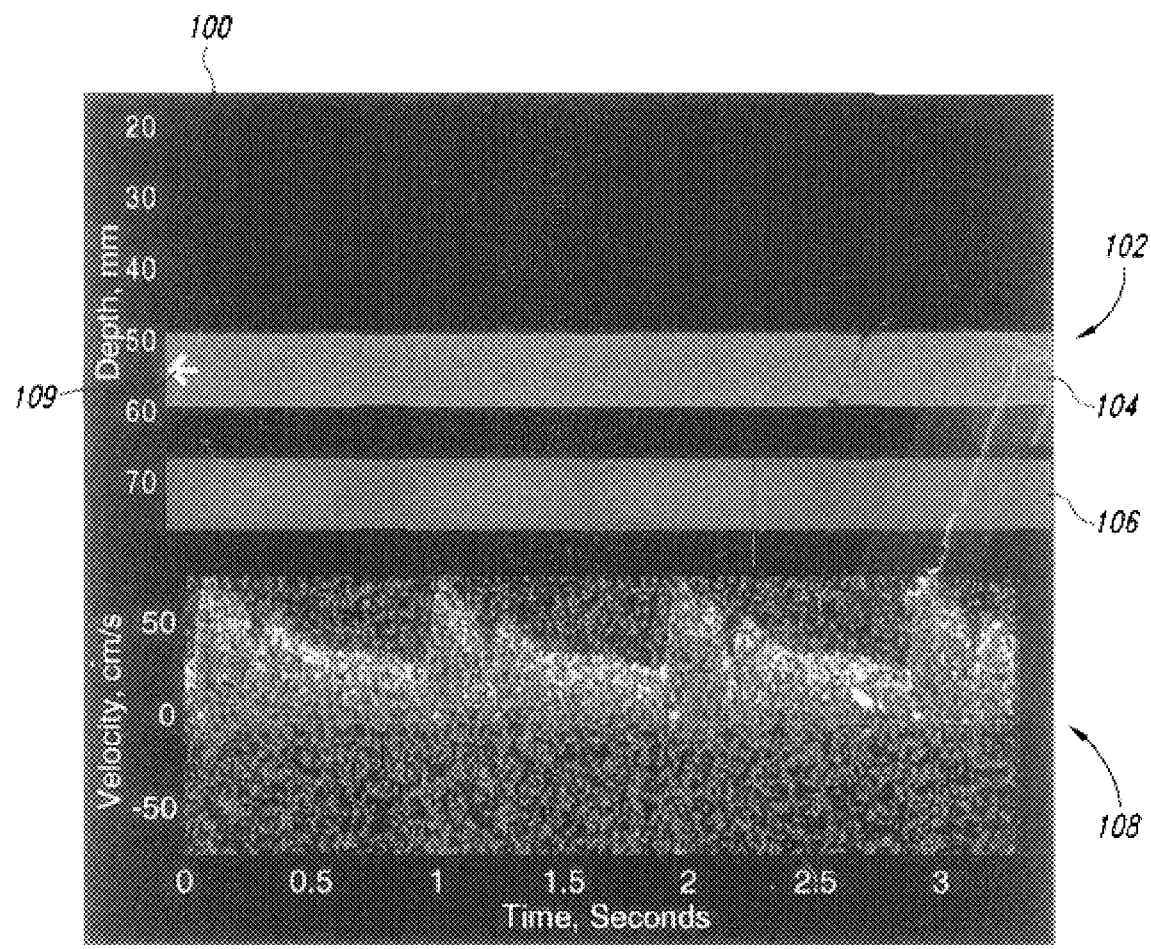
FIG. 4 shows the alternative embodiment of the display mode of FIG. 1 in color.

While the currently preferred embodiment of the depth-mode display 102 employs color intensity mapping as a function of signal intensity, and further colored red or blue according to flow directions towards or away from the probe, those skilled in the art will appreciate that color intensity as a function of detected velocity may be employed instead. In such case, and as shown in FIG. 3, color intensity varies from the clutter cutoff magnitude to a maximum velocity magnitude, corresponding with one-half the pulse repetition frequency (PRF). Detected signals having a power below the noise threshold or above the selected upper power limit are ignored. FIG. 4 is a color figure that shows the Aiming mode display 100 in which the color intensity of the regions 104 and 106 vary as a function of detected velocity. Both the depth-mode display 102 and the spectrogram 108 are displayed relative to the same time axis, and the depth-mode display shows variation both in spatial extent and in color intensity with the same periodicity as the heart beat. Those skilled in the art will also appreciate that instead of varying color intensity solely as a function of signal amplitude or solely as a function of velocity, one could advantageously vary color intensity as a function of both signal amplitude and velocity.

The particularly depicted depth-mode display 102 shown in FIG. 1 shows a simplified display of a single, well-defined red region 104 and a single, well-defined blue region 106. Those skilled in the art will appreciate that the number and characteristics of colored regions will vary depending on ultrasound probe placement and orientation. Indeed, a catalogue of characteristic depth-mode displays can be provided to assist the user in determining whether a particularly desired blood vessel has, in fact, been located. Once the user finds the characteristic depth-mode display for the desired blood vessel, the user can then conveniently determine the depth at which to measure the spectrogram 108.

The Aiming mode 100 enables the user to quickly position the ultrasound probe, such as adjacent to an ultrasound window through the skull so that intracranial blood flow can be detected. Use of colorized representation of signal amplitude is particularly advantageous for this purpose, since a strong signal is indicative of good probe location and orientation. The use of colorized representation of flow velocity may not be as advantageous, except where blood flow velocities vary significantly over blood vessel cross-section. However, when attempting to monitor blood flow near appreciably moving tissue (e.g., cardiac motion above clutter cutoff velocity), colorized representation of flow velocities may be preferred.

Figure 5:
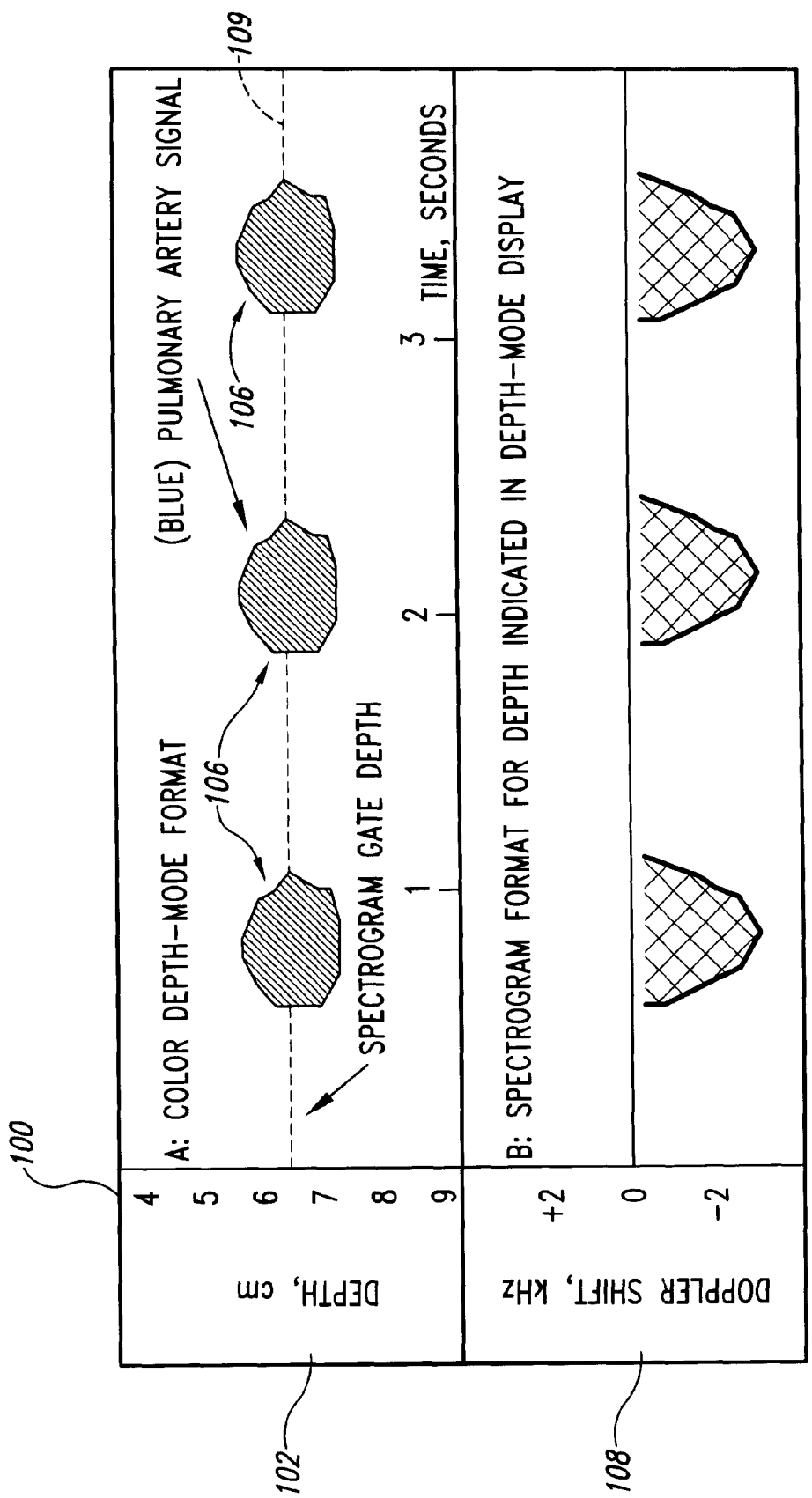
FIG. 5 is a graphical diagram depicting the display mode of FIG. 4 and its use to identify the pulmonary artery.

Referring to FIG. 5, use of the Aiming mode 100 is shown in connection with identifying a particular blood vessel, such as the pulmonary artery or femoral vein. In this case, a colorized representation of flow velocity is advantageously used in the depth-mode display 102, because of the high variation in blood flow velocities in these particular blood vessels. By observing the temporal variation in the depth-mode display 102, and the corresponding spectrogram 108, a user can identify optimal location of the pulmonary artery as follows: (1) the depth-mode display of the pulmonary artery will be blue with the same periodicity as the heart beat; (2) the blue region will typically reside between 4 and 9 cm depth; (3) along the time axis, the blue signal will be relatively intense in the middle of systole, corresponding to peak velocity; and (4) the signal will have the largest vertical extent in the depth-mode display, indicating that the user has positioned the probe such that the longest section of the pulmonary artery is aligned coincident with the ultrasound beam during systole. The user can then adjust other parameters, such as gate depth for the displayed spectrogram 108 and clutter filter parameters.

The Aiming mode 100 also indicates to the user where to set the depth of the pulse Doppler sample gate so that the spectrogram 108 will process Doppler shifts from desired blood flow signals. It is the spectrogram 108 that is of primary clinical interest, allowing the user to observe and measure parameters associated with a particular blood flow and providing information that might suggest hemodynamically significant deviations in that blood flow. Along with the depth-mode display 102 and the correspondingly selected spectrogram 108, the information displayed to a user also typically includes well-known numerical parameters associated with the spectrogram, such as mean peak systolic velocity, mean end diastolic velocity, pulsatility index, and the relative change in mean peak systolic velocity over time. Those skilled in the art will appreciate that other parameters and displays may also be provided, including data provided by other monitoring devices, such as EKG- or EEG-related information.

Figure 6:
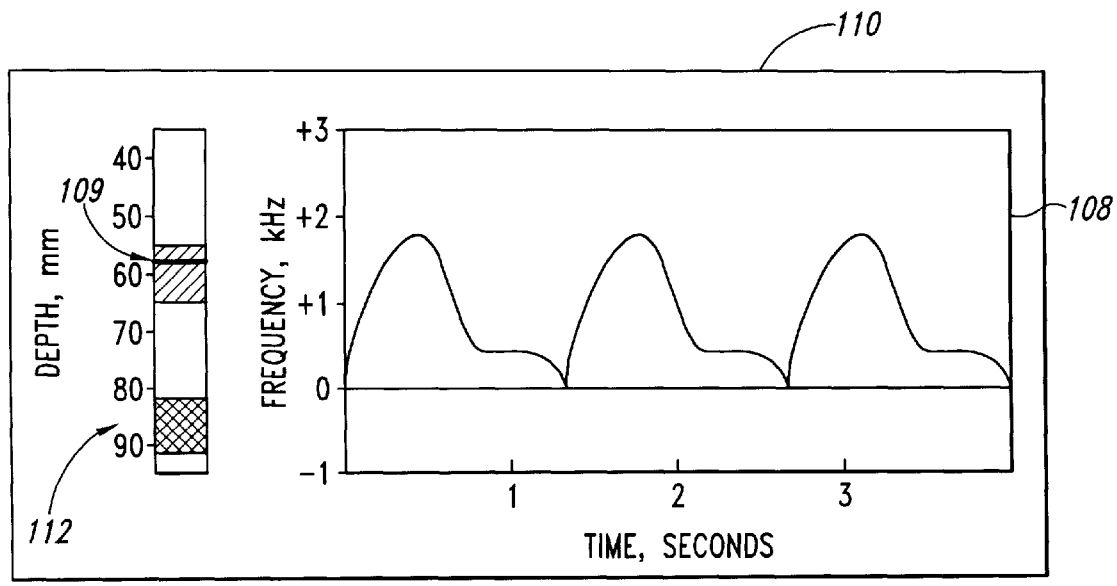
FIG. 6 is a graphical diagram depicting a second Doppler ultrasound system display mode in accordance with an embodiment of the invention.

The Aiming mode display 100 of FIG. 1 is particularly useful in positioning and orienting the Doppler ultrasound probe, and in first selecting a depth at which to measure the spectrogram 108. Following probe location and orientation and range gate selection, the user will typically prefer to have an information display emphasizing the clinically valuable spectrogram 108. Referring to FIG. 6, a second display mode is shown that is referred to as a Spectral mode 110. In this mode, the spectrogram 108 occupies a larger display area. Instead of the full depth-mode display 102, a compressed depth-mode display 112 is provided. This compressed depth-mode display 112, on a shortened time scale, provides information concerning the depth of the sample volume at which the spectrogram 108 is taken, and the status of the blood flow in that sample volume, towards or away from the probe. Thus, the user is continually informed concerning the desired sample volume depth and associated blood flow. This allows for quick understanding and compensation for any changes in the location of the desired sample volume relative to the blood flow, such as due to probe motion. This also allows a user of the ultrasound system to fine tune the sample volume depth even while focusing primary attention on the clinically important spectrogram 108.

Figure 7:
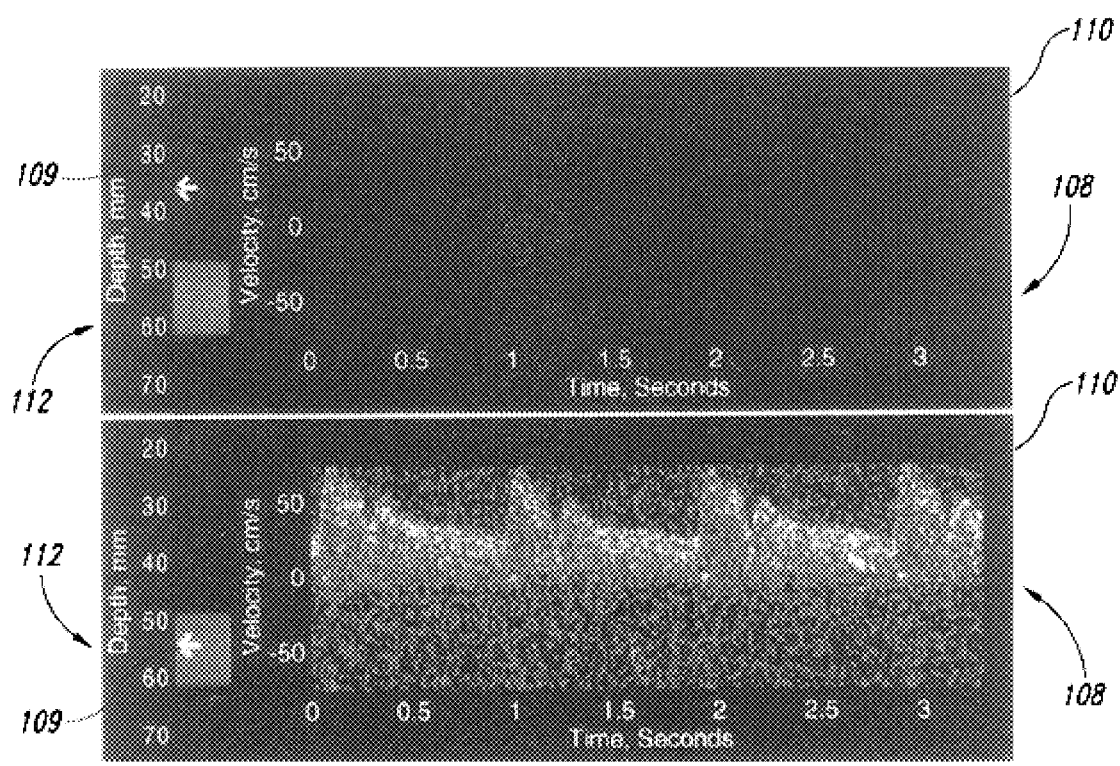
FIG. 7 shows two views of the display mode of FIG. 6 in color.

FIG. 7 shows two different views of the Spectral mode 110 in color. In one view, the selected depth indicated by the pointer 109 in the compressed depth-mode display 112 is not a location at which blood flows, and consequently no there are no blood flow signals in the displayed spectrogram 108. In the other view, the selected depth indicated by the pointer 109 does coincide with blood flow, and a corresponding spectrogram 108 is displayed. In the particular embodiment shown in FIG. 7, the color intensity of the region 104 varies as a function of detected velocity, and shows a characteristic color variation that may be associated with variation in blood velocity across blood vessel cross-section, a variation with depth in the alignment of the detected blood flow relative to the ultrasound beam axis, or both.

Those skilled in the art will appreciate the important advantages provided by the diagnostic information displays shown in FIGS. 1, 4, 6, and 7. While the displayed spectrogram 108 is not itself new, today's pulse Doppler ultrasound systems that do not have B-mode capability lack a means for successfully and reliably locating and orienting an ultrasound probe and determining an appropriate sample volume depth at which to detect the blood flow of interest. Also, while colorized representation of blood flow directions and speeds or signal amplitude is well known in the art, such as in color M-mode displays, such displays have not been used for the purpose of aiming ultrasound probes or in selecting particular sample volume depths for concurrent spectrogram analysis.

Figure 8:
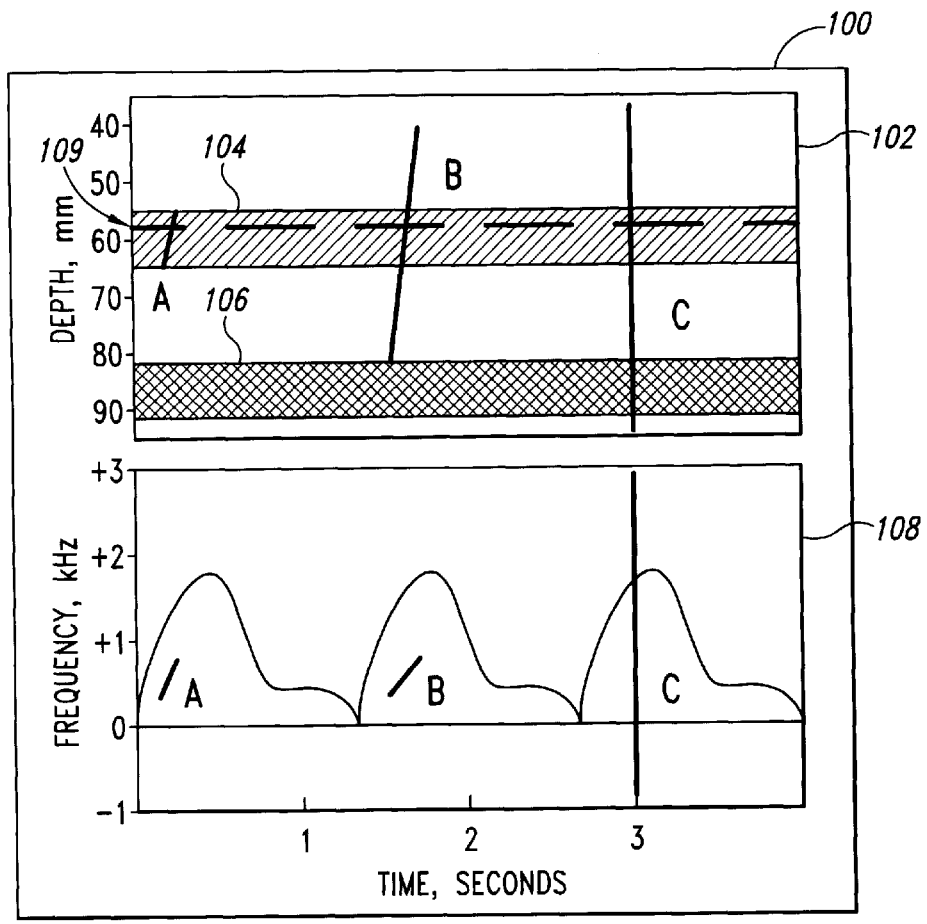
FIG. 8 is the graphical diagram of the display mode shown in FIG. 1, further depicting and distinguishing embolic signals from artifact signals.

Referring to FIG. 8, the simultaneous presentation of the depth-mode display 102 and spectrogram 108 can also provide important information for detecting embolic signals and differentiating such signals from non-embolic artifacts. FIG. 8 depicts three events: A, B, and C. In event A, the depth-mode display 102 shows a particularly high intensity signal having a non-vertical slope—i.e., a high-intensity signal that occurs at different depths at different times. In event A, the signal exists only within the boundary of one of the colored blood flow regions 104 and 106. In the spectrogram 108, a particularly high intensity signal is seen to have different velocities, bounded by the maximum flow velocity, within a short temporal region within the heartbeat cycle. Event A is strong evidence of an embolus passing through a blood flow region near the selected sample volume.

Event B is another likely candidate for an embolus. In this case, the high-intensity signal seen in the depth-mode display 102 is non-vertical, but does not appear exclusively within a range of depths where blood is flowing. While this signal is strong enough and/or has a long enough back scatter to appear outside the blood flow margin in the depth-mode display 102, the spectrogram display 108 still shows the characteristic high intensity transient signal associated with an embolus. Event B is also evidence of an embolus, but likely an embolus different in nature from that associated with event A. Although the particular signal characteristics of various emboli have not yet been fully explored in the depth-mode display, the distinction between events A and B is likely that of different embolus types. For example, event A may be associated with a particulate embolus, whereas event B may be associated with a gaseous embolus, with the different acoustic properties of a gas bubble causing the particularly long back scatter signal and the appearance of occurrence outside the demonstrated blood flow margins.

Event C is an artifact, whether associated with probe motion or some other non-embolic event. Event C appears as a vertical line in the depth-mode display 102, meaning that a high-intensity signal was detected at all depth locations at precisely the same time—a characteristic associated with probe motion or other artifact. Similarly, the high-intensity signal displayed in the spectrogram display 108 is a vertical line indicating a high-intensity signal detected for a wide range of velocities (including both positive and negative velocities and velocities in excess of the maximum blood flow velocities) at precisely the same time. Event C then is readily characterized as an artifact signal, and not embolic in nature.

Those skilled in the art will appreciate that the simultaneous display of the depth-mode display 102 and the spectrogram 108 provides not only convenient means for locating the desired sample volume, but also provides a particularly useful technique for distinguishing embolic signals from artifact signals, and perhaps even for characterizing different embolic signals. Such embolic detection and characterization is easily observed by the operator, but can also be automatically performed and recorded by the ultrasound apparatus.

Automatic embolus detection is provided by observing activity in two or more sample gates within the blood flow at the same time. The system discriminates between two different detection hypotheses:

(1) If the signal is embolic, then it will present itself in multiple sample gates over a succession of different times.

(2) If the signal is a probe motion artifact, then it will present itself in multiple sample gates simultaneously.

These two hypotheses are mutually exclusive, and events that are declared embolic are done so after passing the "Basic Identification Criteria of Doppler Microembolic Signals" (see, for example, *Stroke*, vol. 26, p. 1123, 1995) and verifying that successive detection (by time-series analysis or other suitable technique) of the embolic signal in different sample gates is done at different points in time, and that the time delay is consistent with the direction of blood flow. The differentiation of embolic from artifact signals can be further confirmed by also observing activity at one or more sample gates outside the blood flow.

Figure 9:
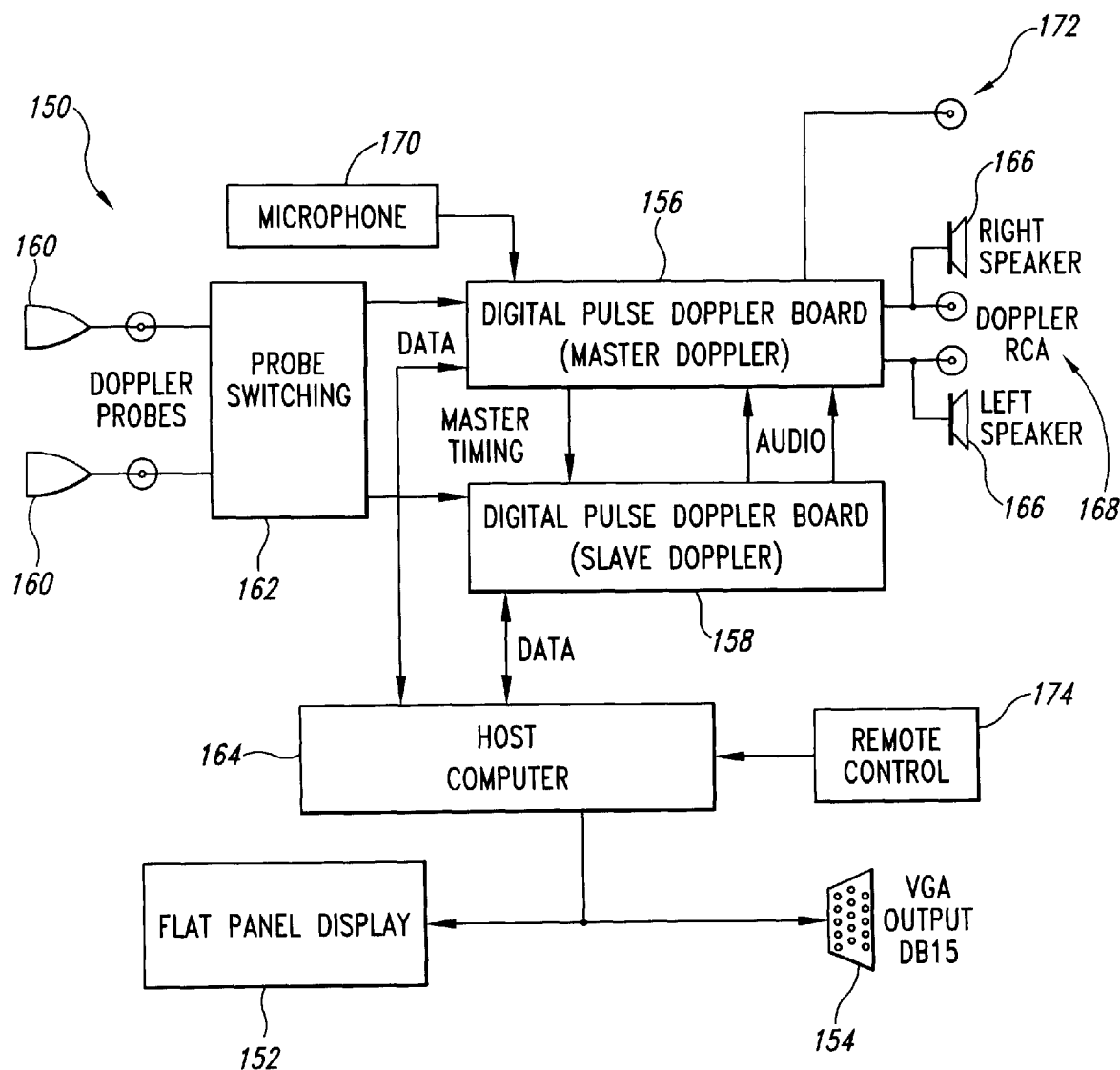
FIG. 9 is a functional block diagram depicting a Doppler ultrasound system in accordance with an embodiment of the invention.

FIG. 9 is a functional block diagram that depicts an ultrasound system 150 in accordance with an embodiment of the invention. The ultrasound system 150 produces the various display modes described above in connection with FIGS. 1–8 on an integrated flat panel display 152 or other desired display format via a display interface connector 154. The signal processing core of the Doppler ultrasound system 150 is a master pulse Doppler circuit 156 and a slave pulse Doppler circuit 158. The Doppler probes 160 are coupled with other system components by a probe switching circuit 162. The probe switching circuit 162 provides both presence-detect functionality and the ability to distinguish between various probes, such as by detecting encoding resistors used in probe cables or by other conventional probe-type detection. By providing both the master and slave pulse Doppler circuits 156 and 158, two separate ultrasound probes 160 may be employed, thereby providing unilateral or bilateral ultrasound sensing capability (such as bilateral transcranial measurement of blood velocity in the basal arteries of the brain). The master and slave pulse Doppler circuits 156 and 158 receive the ultrasound signals detected by the respective probes 160 and perform signal and data processing operations, as will be described in detail below. Data is then transmitted to a general purpose host computer 164 that provides data storage and display. A suitable host computer 164 is a 200 MHz Pentium processor-based system having display, keyboard, internal hard disk, and external storage controllers, although any of a variety of suitably adapted computer systems may be employed.

The ultrasound system 150 also provides Doppler audio output signals via audio speakers 166, as well as via audio lines 168 for storage or for output via an alternative medium. The ultrasound system 150 also includes a microphone 170 for receipt of audible information input by the user. This information can then be output for external storage or playback via a voice line 172. The user interfaces with the ultrasound system 150 primarily via a keyboard or other remote input control unit 174 coupled with the host computer 164.

Figure 10:
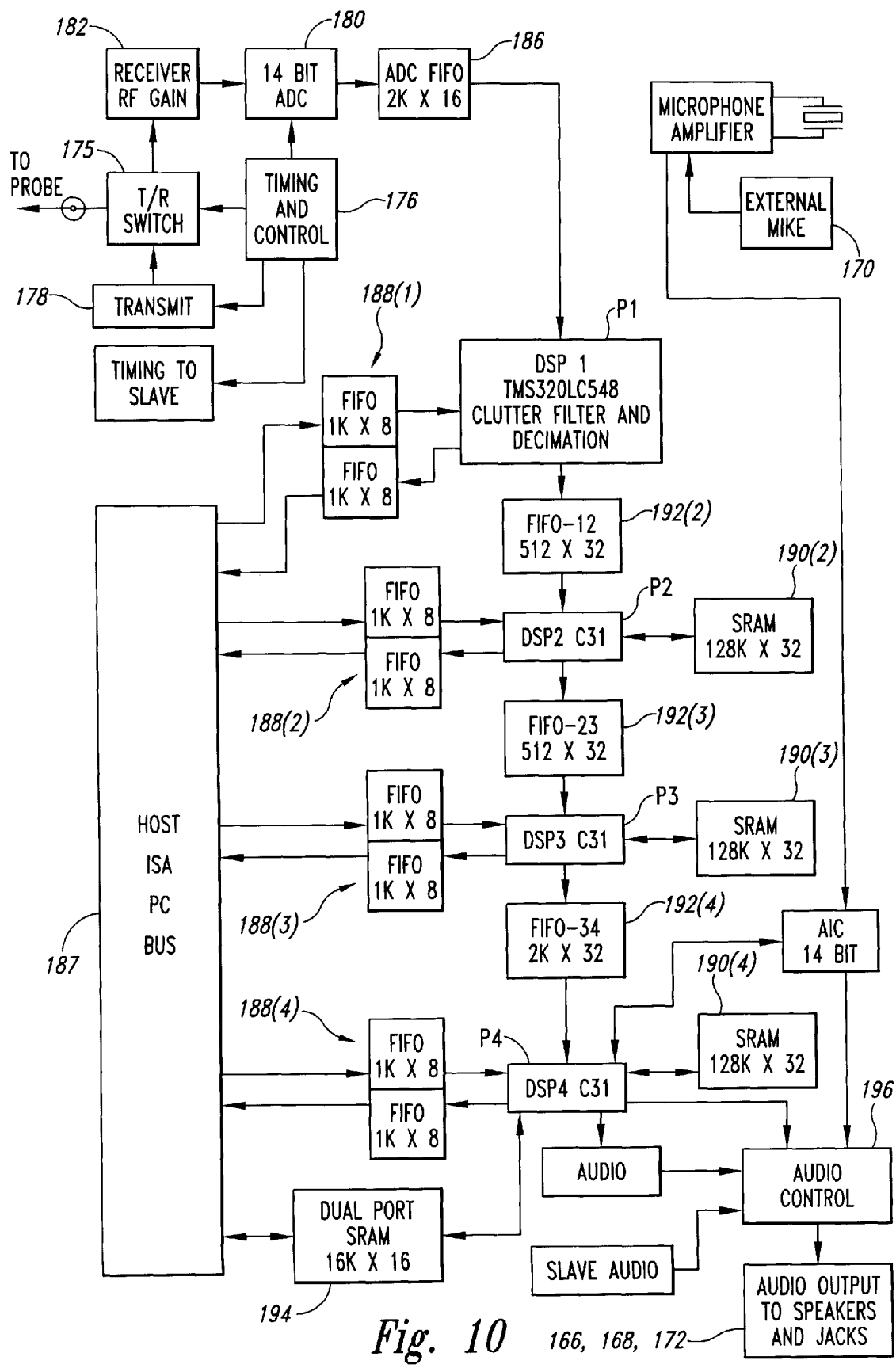
FIGS. 10 and 11 are functional block diagrams depicting particular details of pulse Doppler signal processing circuitry included in the Doppler ultrasound system of FIG. 9.
Figure 11:
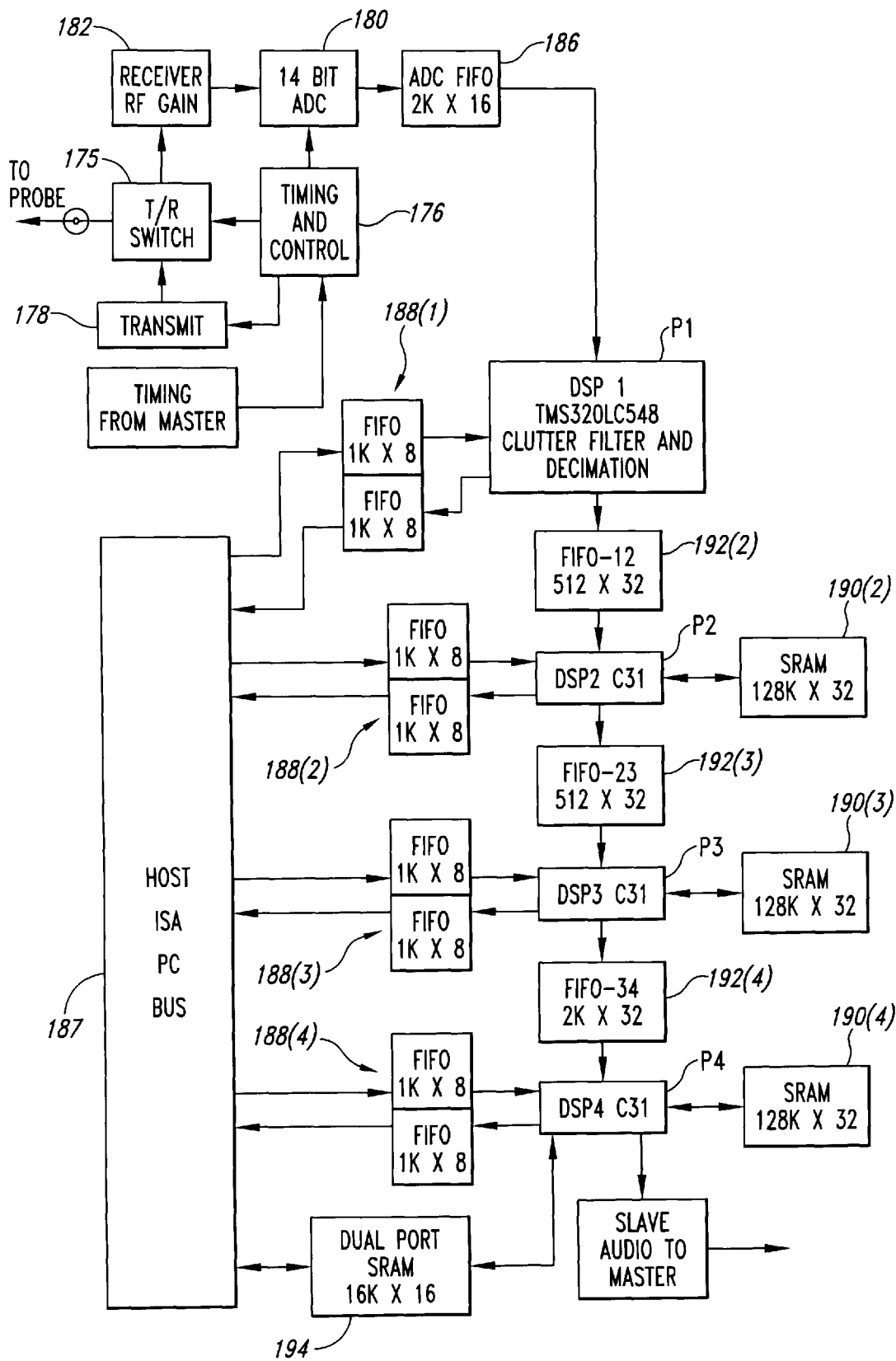

FIGS. 10 and 11 depict particular details of the master and slave pulse Doppler circuits 156 and 158. To the extent FIGS. 10 and 11 depict similar circuit structures and interconnections, these will be described once with identical reference numbers used in both Figures. FIG. 10 also depicts details concerning the input and output of audio information to and from the ultrasound system 150 via the microphone 170, the speakers 166, and the audio output lines 168 & 172, the operations of which are controlled by the master pulse Doppler circuit 156.

At the transducer input/output stage, each of the pulse Doppler circuits 156 and 158 includes a transmit/receive switch circuit 175 operating under control of a timing and control circuit 176 (with the particular timing of operations being controlled by the timing and control circuit 176 of the master pulse Doppler circuit 156). The timing and control circuit 176 also controls operation of a transmit circuit 178 that provides the output drive signal causing the Doppler probes 160 (see FIG. 9) to emit ultrasound. The timing and control circuit 176 also controls an analog-to-digital converter circuit 180 coupled to the transmit/receive switch 175 by a receiver circuit 182. The function and operation of circuits 175–182 are well known to those skilled in the art and need not be described further.

The primary signal processing functions of the pulse Doppler circuits 156 and 158 are performed by four digital signal processors P1–P4. P1 is at the front end and receives digitized transducer data from the receiver 182 via the analog-to-digital converter circuit 180 and a data buffer circuit or FIFO 186. P4 is at the back end and performs higher level tasks such as final display preparation. A suitable digital signal processor for P1 is a Texas Instruments TMS320LC549 integer processor, and suitable digital signal processors for P2–P4 are Texas Instruments TMS320C31 floating point processors, although other digital signal processing circuits may be employed to perform substantially the same functions in accordance with the invention.

Received ultrasound signals are first processed by the digital signal processor P1 and then passed through the signal processing pipeline of the digital signal processors P2, P3, and P4. As described in detail below, the digital signal processor P1 constructs quadrature vectors from the received digital data, performs filtering operations, and outputs Doppler shift signals associated with 64 different range gate positions. The digital signal processor P2 performs clutter cancellation at all gate depths. The digital signal processor P3 performs a variety of calculations, including autocorrelation, phase, and power calculations. P3 also provides preparation of the quadrature data for stereo audio output. The digital signal processor P4 performs most of the calculations associated with the spectrogram display, including computation of the spectrogram envelope, systole detection, and also prepares final calculations associated with preparation of the Aiming display.

Each of the digital signal processors P1–P4 is coupled with the host computer 164 (see FIG. 9) via a host bus 187 and control data buffer circuitry, such as corresponding FIFOs 188(1)–188(4). This buffer circuitry allows initialization and program loading of the digital signal processors P1–P4, as well as other operational communications between the digital signal processors P1–P4 and the host computer. Each of the digital signal processors P2–P4 is coupled with an associated high-speed memory or SRAM 190(2)–190(4), which function as program and data memories for the associated signal processors. In the particularly depicted signal processing chain of FIG. 10 or 11, the digital signal processor P1 has sufficient internal memory, and no external program and data memory need be provided. Transmission of data from one digital signal processor to the next is provided by intervening data buffer or FIFO circuitry 192(2)–192(4). The ultrasound data processed by the digital signal processor P4 is provided to the host computer 164 via data buffer circuitry such as a dual port SRAM 194.

Referring to FIG. 10, the digital signal processor P4 of the master pulse Doppler circuit 156 also processes audio input via the microphone 170, as well as controlling provision of the audio output signals to the speakers 166 and audio output lines 168, 172. P4 controls the audio output signals by controlling operations of an audio control circuit 196, which receives audio signals from both the master and the slave pulse Doppler circuits 156 and 158.

Referring to process flow charts shown in FIGS. 12–16, a detailed description will now be provided of the operations performed by of each of the digital signal processors P1–P4 included in both the master and slave pulse Doppler circuits 156 and 158. Particular detailed calculations and numerical information are provided to disclose a current embodiment of the invention, but those skilled in the art will appreciate that these details are exemplary and need not be included in other embodiments of the invention.

Figures 12, 13:
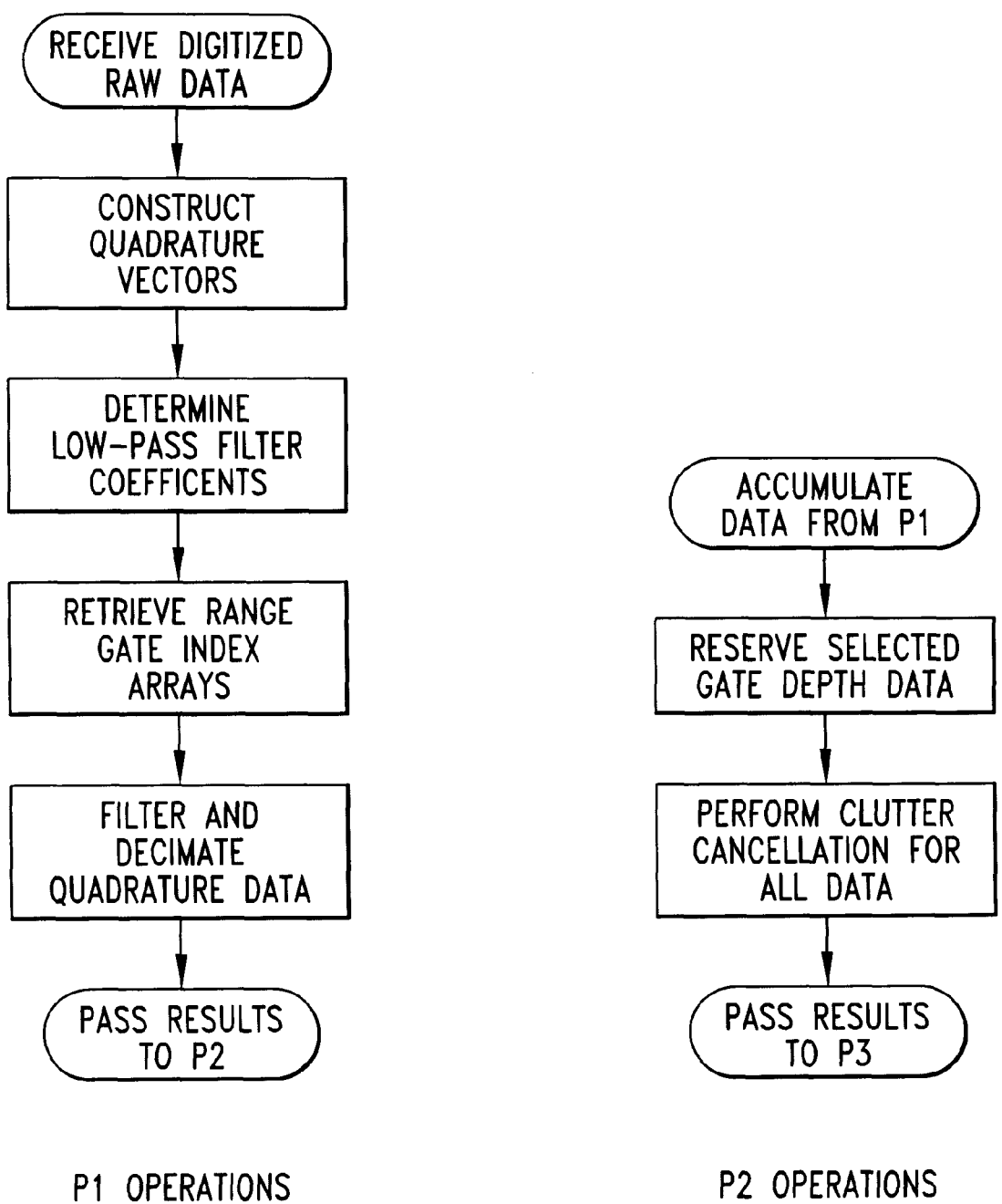
FIGS. 12–16 are process flow charts depicting particular operations performed by the pulse Doppler signal processing circuitry of FIGS. 10 and 11.

Referring to FIG. 12, the operations of digital signal processor P1 are as follows:
1. DIGITIZATION OF RAW DATA. Read A(1:N), a series of N 14-bit values from the input A/D. The values are converted at 4× the Doppler carrier frequency (8 MHz), and commence synchronously with the start of the transmit burst. N=1000 if the Doppler pulse repetition frequency (PRF) is 8 kHz, 1280 if the Doppler PRF is 6.25 kHz, and 1600 if the Doppler PRF is 5 kHz.
2. QUADRATURE VECTOR CONSTRUCTION. Construct two vectors with N/4 points each according to the following rules: Br(1:N/4)=A(1:4:N−3)−A(3:4:N−1), and Bi(1:N/4)=A(2:4:N−2)−A(4:4:N). Br and Bi are the digitally demodulated quadrature Doppler values for a series of N/4 different gate depths. The subtractions here remove DC bias from the data.
3. LOW-PASS FILTER COEFFICIENTS. Br and Bi contain frequencies up to carrier/4, and need to be further filtered to remove noise outside the bandwidth of the Doppler transmit burst. The coefficients for accomplishing this low-pass filtering are determined by a creating, with standard digital filter design software such as MATLAB, an order 21 low-pass FIR filter. The normalized cutoff of this filter is 2/(T*fs), where T is the time duration of the transmit burst, and fs is the sample rate of the data in Br and Bi (2 MHz). Call this filter C(1:21). The coefficients of this filter will vary as the transmit burst length is changed by the user, and a bank of several different sets of filter coefficients is accordingly stored to memory.
4. INDEX ARRAYS. Data from 64 range gate positions are to be processed and passed onto P2. For ease of graphical display, these range gate positions are selected to be 1 mm apart. However, the quadrature vectors Br and Bi do not contain elements that are spaced 1 mm apart—they are 0.385 mm apart. Therefore, indices into the Br and Bi arrays are used that correspond to values falling closest to multiples of 1 mm, as a means to decimating Br and Bi to 1 mm sampling increments. This is done by having a prestored array of indices, D1(1:64), corresponding to depths 29:92 mm for 8 kHz PRF, and indices D2(1:64) and D3(1:64) with corresponding or deeper depth ranges for 6.25 kHz and 5 kHz PRFs.
5. LOW-PASS FILTER AND DECIMATION OF QUADRATURE DATA. The Br and Bi arrays are low-pass filtered and decimated to 64 gates by the following rules (note <a,b> is the 32 bit accumulated integer dot product of vectors a and b):
   8 kHz PRF:
   Er(j)=<C, Br(D1(j)+(−10:10))>
   Ei(j)=<C, Bi(D1(j)+(−10:10))>, and j=1:64.
   6.25 kHz PRF:
   Er(j)=<C, Br(D2(j)+(−10:10))>
   Ei(j)=<C, Bi(D2(j)+(−10:10))>, and j=1:64.
   5 kHz PRF:
   Er(j)=<C, Br(D3(j)+(−10:10))>
   Ei(j)=<C, Bi(D3(j)+(−10:10))>, and j=1:64.
6. PASS RESULTS TO P2. Er and Ei, 128 values altogether, comprise the Doppler shift data for 1 pulse repetition period, over a set of 64 different sample gates spaced approximately 1 mm apart. These arrays are passed to P2 with each new transmit burst.

Referring to FIG. 13, the operations of digital signal processor P2 are as follows:
1. ACCUMULATE INPUT DATA. Collect a buffer of M Er and Ei vectors from P1 over a period of 8 ms, into floating point matrices Fr and Fi. At the PRFs of [8,6.25,5]kHz, the matrices Fr and Fi will each contain respectively M=[64,50,40] vectors. The jth Er and Ei vectors at their respective destinations are denoted by Fr(1:64,j) and Fi(1:64,j) (these are column vectors). The kth gate depth across the M collected vectors is indexed by Fr(k,1:M) and Fi(k,1:M) (these are row vectors).
2. PRESERVATION OF RAW DATA AT "CHOSEN" GATE DEPTH. Reserve in separate buffer the raw data at the user-chosen gate depth, k, at which the Doppler spectrogram is processed. This row vector data, Gr(1:M)=Fr(k,1:M) and Gi(1:M)=Fi(k,1:M), is passed forward to P3 and eventually to the host for recording purposes.
3. CLUTTER CANCELLATION. Apply a fourth order clutter cancellation filter to each row of Fr and Fi. Hr(1:64,1:M) and Hi(1:64,1:M) are the destination matrices of the filtered Fr(1:64,1:M) and Fi(1:64,1:M) data. Application of this filter with continuity requires maintaining state variables and some previous Fr and Fi values. The coefficients of the clutter filter will vary depending on the user choice of [Low Boost, 100 Hz, 200 Hz, 300 Hz, and High Boost]. These coefficients are available by table lookup in processor RAM, given the user choice from the above options.
4. PASS RESULTS TO P3. Gr, Gi, Hr and Hi are passed to P3 for further processing.

Figure 14:
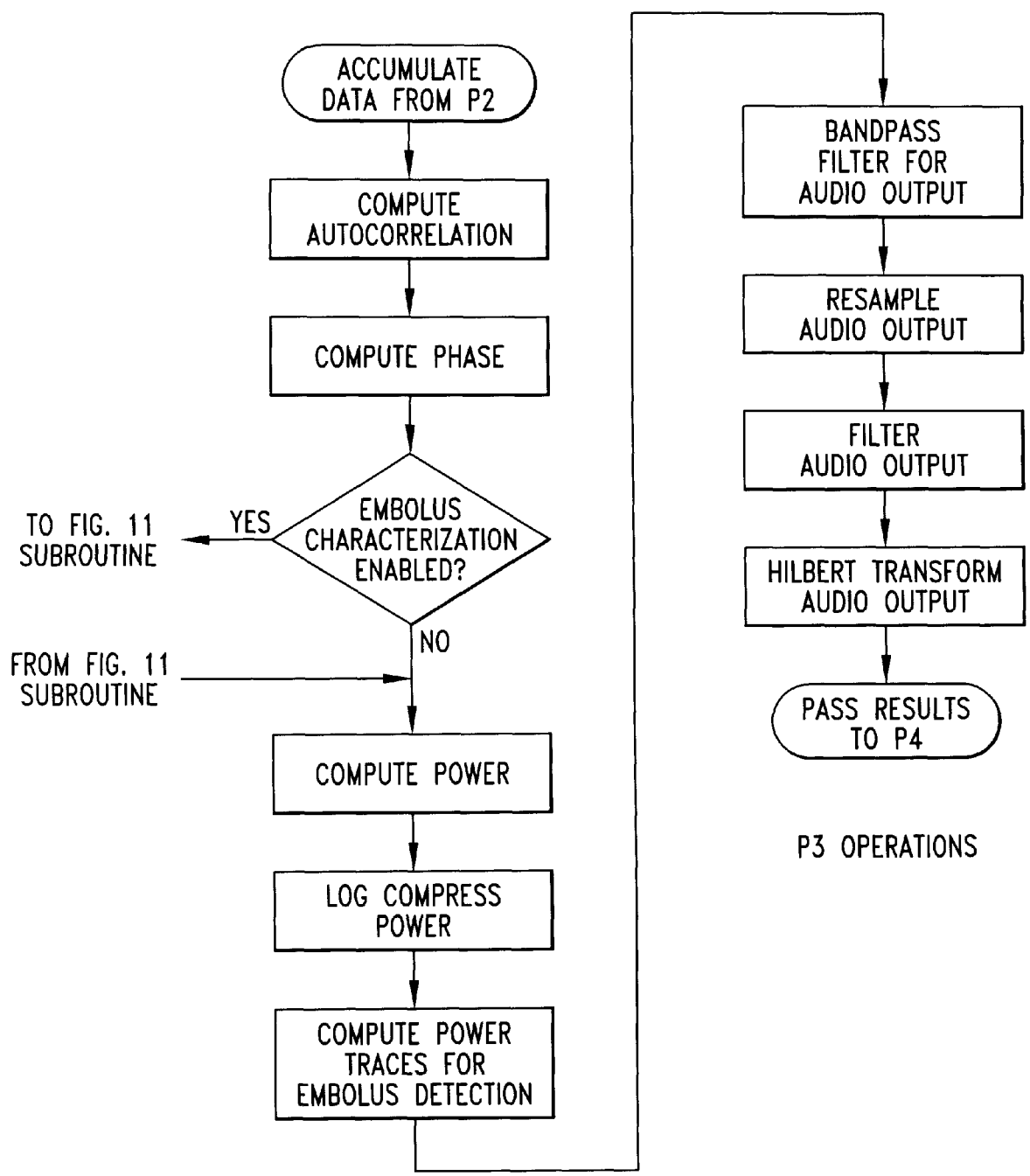

Referring to FIG. 14, the operations of digital signal processor P3 are as follows:
1. ACCUMULATE INPUT DATA. Receive Gr, Gi, Hr and Hi from P2.
2. COMPUTE AUTOCORRELATION. Compute the first lag of the autocorrelation of the data at each gate over time. Use all M values at each gate in this calculation. This will generate an array of 64 complex values, one for each gate. For the kth gate depth, let P=Hr(k,1:M)+jHi (k,1:M). Then the first lag autocorrelation for this depth is AC(k)=<P(1:M−1),P(2:M)>. (Note that in a dot product of complex values, the second vector is conjugated. Also note that this and all dot products in P2, P3, or P4 are floating point calculations.) In this manner, construct the complex vector AC(1:64).

3. COMPUTE PHASE FOR EACH AC VALUE. For each autocorrelation value, us a four quadrant arctangent lookup to determine the phase of the complex value. Specifically, ANGLE(k)=arctan(imag(AC(k)), real(AC(k))). The ANGLE(k) value is proportional to the mean flow velocity at the gate depth k.

4. If embolus characterization (e.g., distinguishing a particle from a bubble) capability is enabled, the method routes to a subroutine described below in connection with FIG. 16.

5. COMPUTE POWER. Compute the signal power. Use all M values at each gate in this calculation. This will generate an array of 64 real values, one for each gate. For the kth gate depth, again let P=Hr(k,1:M)+jHi(k,1:M). Then the power for this depth is POWER(k)=<P(1:M),P(1:M)> (note that in a dot product of complex values, the second vector is conjugated). In this manner, construct the real vector POWER(1:64).

6. LOG COMPRESS POWER. Convert POWER to Decibels: POWERd(1:64)=10*log10(POWER(1:64)).

7. COMPUTE POWER TRACES FOR EMBOLUS DETECTION. For each of four preset gate depths (one being the user selected depth and the other three being correspondingly calculated), compute power from a 60 point moving window at M different positions of the window. Note that some history of the data at the specific gate depths will be required to maintain this calculation without interruption from new data spilling in every 8 ms. Specifically, for gate n, POWER_TRACEn(i)=<Hr(n,i−59:i)+jHi(n,i−59:i), Hr(n,i−59:i)+jHi(n,i−59:i)>. Note 3 power traces are taken from the region including the sample volume placed inside blood flow, while the fourth power trace is taken from a sample volume well outside the blood flow.

8. COMPLEX BANDPASS FILTER FOR USE IN AUDIO OUTPUT PREPARATION. The min and max frequencies resulting from user specified spectral unwrapping of the spectrogram are used to determine a complex bandpass filter for making the audio output sound congruent with what is shown on the spectrogram display. For example, if the unwrapping occurs at [−1,7]kHz, then the audio complex bandpass filter has edges at −1 kHz and +7 kHz. A bank of several sets of complex bandpass filter coefficients, corresponding to different unwrap ranges, is generated offline and placed in memory. Each coefficient set corresponds to one of the unwrapping selections the user can make. Let the operative set of filter coefficients be called UWa(1:O) and UWb(1:O), where O is the filter order plus one.

9. AUDIO OUTPUT PREPARATION: RESAMPLE. At the gate depth selected by the user, k, the Doppler shift signals are to be played out the audio speakers. Before doing so, some prepping of the audio signals is important to match the user-selected spectral unwrapping. Resample the audio signal Hr(k,1:M) and Hi(k,1:M) to twice the PRF by multiplexing the respective arrays with zeros: Qr(k,1:2M)={Hr(k,1), 0, Hr(k,2), 0, Hr(k,3), 0, . . . , Hr(k,M), 0} and Qi(k,1:2M)={Hi(k,1), 0, Hi(k,2), 0, Hi(k,3), 0, . . . , Hi(k,M), 0}.

10. AUDIO OUTPUT PREPARATION: COMPLEX BANDPASS. Apply a complex bandpass filter to Qr+jQi in order to remove the extra images introduced by multiplexing the data with zeros:

R(n)=UWb(1)*Q(n)+UWb(2)*Q(n−1)+ . . . +UWb(O)*Q(n−O+1)−Uwa(2)*R(n−1)−Uwa(3)*R(n−2)− . . . −Uwa(O)*R(n−O+1)

where Q(k)=Qr(k)+jQi(k).

11. AUDIO OUTPUT PREPARATION: HILBERT TRANSFORM. The audio data in the sequence R(n) is in quadrature format and needs to be converted into stereo left and right for playing to the operator. This is done with a Hilbert transform, and a 95 point transform, H(1:95), is used in this work—the coefficients can be obtained with formulas in the literature or standard signal processing software such as MATLAB. The application of the Hilbert transform to a data sequence is done as an FIR filter. Construction of stereo separated signals RL and RR from R(n) is done according to [RL=Hilbert(Rr)+Delay(Ri), RR=Hilbert(Rr)−Delay(Ri)] where Delay is a (Nh+1)/2 step delay of the imaginary component of R, and Nh is the size of the Hilbert filter (95).

Figure 15:
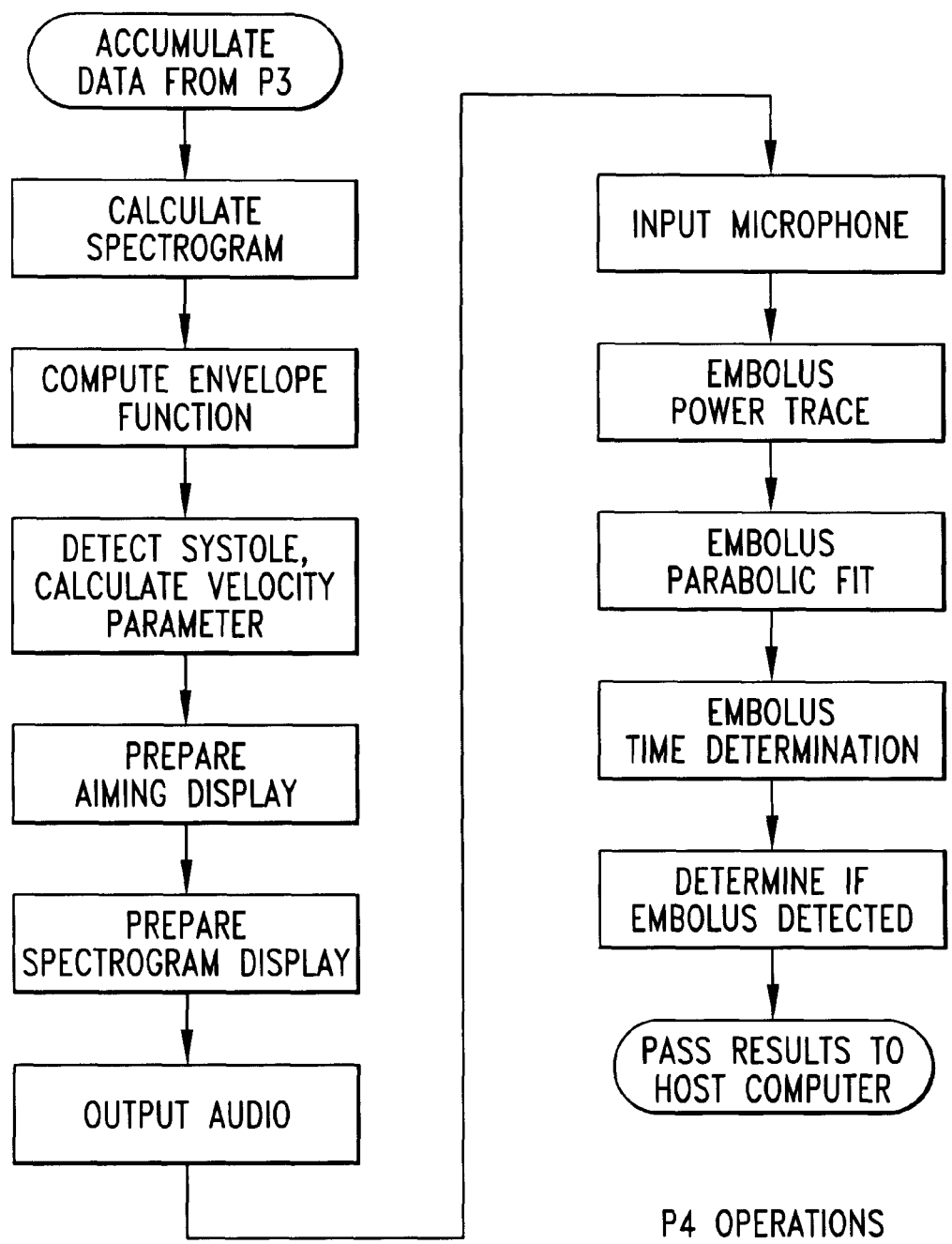

12. Pass Gr, Gi, ANGLE, POWERd, POWER_TRACE1, POWER_TRACE2, POWER_TRACE3, POWER_TRACE4, Rr, Ri, RL and RR to P4 for further processing. Referring to FIG. 15, the operations of digital signal processor P4 are as follows:

1. ACCUMULATE INPUT DATA. Receive Gr, Gi, ANGLE, POWERd, POWER_TRACE1, POWER_TRACE2, POWER_TRACE3, POWER_TRACE4, Rr, Ri, RL and RR from P3.

2. CALCULATE SPECTROGRAM. Compute power spectrum via the following steps: a) Concatenate new points in the Rr+jRi sequence with old points such that there are 128 points altogether, b) Multiply the 128 point sequence against a 128 point Hanning window, c) Calculate P, the FFT of the 128 point sequence, d) Calculate Pd=10*log10(P), and e) FFTSHIFT the Pd sequence such that DC is at its center.

3. ENVELOPE. Compute the maximum frequency follower or "envelope" function, E(j), which indicates the upper edge of the flow signals in the spectrogram. This is an integer between 0 and 63, and is indexed by FFT calculation—i.e., for every spectral line calculation there is one value of E. Those skilled in the art will know of a variety of algorithms for making this calculation.

4. SYSTOLE DETECTION. Based on the maximum frequency follower, detect the start of systole. When the systolic start has been determined, set SYSTOLE_FLAG=TRUE. Also calculate the end diastolic velocity value, VEND, the peak systolic velocity value, VPEAK, and the mean velocity, VMEAN.

5. AIMING DISPLAY PREPARATION. Prepare the Aiming display via the following steps: a) Subtract the value of the "aim noise" parameter set by the user from the POWERd array: POWERd2=POWERd−aim_noise, b) multiply POWERd2 by a factor which is 64 (the number of color shades) divided by the value of the "aim range" parameter set by the user—POWERd3=POWERd2*64/aim_range, c) clip the resulting power data at 0 on the low end and 63 on the high end—the values now correspond to entries in a 64-value red or blue color table, and place results in array POWERd4, and d) multiply each of the power values by 1, 0 or −1, depending respectively on whether the associated ANGLE value is greater than the "filter cutoff parameter", less in absolute value than the filter cutoff parameter, or less than the negative of the filter cutoff parameter. This results in 64 values (one per gate depth) in the range of [−64,+63]. This modified aiming array, POWERd5, is ready to display after sending to the host computer.

6. SPECTROGRAM DISPLAY PREPARATION. Prepare the spectrogram display via the following steps: a) Subtract the user-selected noise floor parameter from the array Pd—Pd2=Pd-spectral_noise, b) Rescale the spectral data to contain 256 colors across the user-specified dynamic range—Pd3=Pd2*256/spectral_range, c) truncate/clip the data to be integer valued from 0 to 255—Pd4=min(255,floor(Pd3)), d) truncate the data to 8 bits—Pd5=8 bit truncate(Pd4).
7. AUDIO OUTPUT. Send the arrays RR and RL, the right and left speaker audio outputs, to the speakers via port writes.
8. INPUT MICROPHONE. Sample M values into vector MIC from the input microphone port (M is # of transmit pulse repetitions within an 8 ms period).
9. EMBOLUS DETECTION: BACKGROUND POWER IN POWER TRACES. For each of the four power traces, POWER_TRACE1 ... POWER_TRACE4, corresponding to the four preset gate depths, compute a background power level. Recall that POWER_TRACEn contains M values, where M is # of transmit pulse repetitions within an 8 ms period). The background power value is obtained by a delta-follower for each trace, and is denoted by $\delta 1$, $\delta 2$, $\delta 3$, and d $\delta 4$.

$\delta 1 new = \delta 1 old + \Delta$, where $\Delta = sign(\delta 1 old - mean(POWER\_TRACE1))*0.1$ dB.

$\delta 2 new = \delta 2 old + \Delta$, where $\Delta = sign(\delta 2 old - mean(POWER\_TRACE2))*0.1$ dB.

$\delta 3 new = \delta 3 old + \Delta$, where $\Delta = sign(\delta 3 old - mean(POWER\_TRACE3))*0.1$ dB.

$\delta 4 new = \delta 4 old + \Delta$, where $\Delta = sign(\delta 4 old - mean(POWER\_TRACE4))*0.1$ dB.

This update in the background values is done once every M power values, or every 8 ms.
10. EMBOLUS DETECTION: PARABOLIC FIT. Apply a parabolic fit algorithm to the power trace each gate and determine if an event is occurring during the 8 ms period. This fit must be applied to successive data windows spaced apart by at most 1 ms. If the parabolic fit is concave down, and has a peak that exceeds the background power for the gate depth by 6 dB (an arbitrary threshold), then an event is detected.
11. EMBOLUS DETECTION: TIME DETERMINATION. For any single-gate events, compute the exact time of the event by analyzing the power trace between the –6 dB points on either side of the peak power of the event. Record event results and times so that current events may be compared to past ones.
12. EMBOLUS DETECTION: HIGH LEVEL CALCULATION. If the following conditions are true, then set DETECTION=TRUE: a) at least two adjacent of three gates in vicinity of blood flow show events within a 40 ms time window, b) the gate outside the blood flow shows no detection, and c) the timing of events shows progression in the direction of blood flow (i.e., the embolus is not swimming upstream).
13. Pass Gr, Gi, POWERd5, Pd5, SYSTOLE_FLAG, VEND, VMEAN, VPEAK, MIC and DETECTION to host for further processing.

Figure 16:
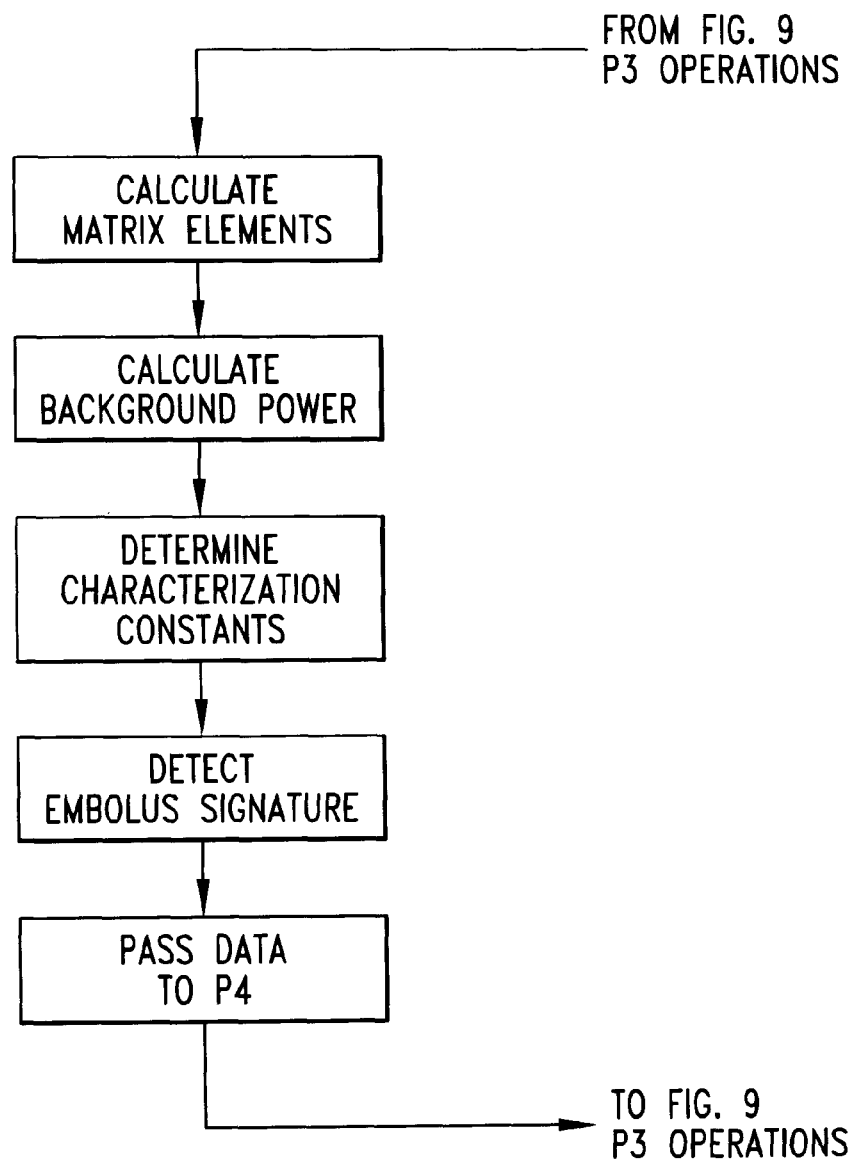

Referring to FIG. 16, the embolus characterization subroutine operations of digital signal processor P3 are as follows:
4A. CALCULATE MATRIX ELEMENT MAGNITUDES of Hr+jHi: Hmag(1:64,1:M)=10*log10(Hr.^2+Hi.^2).
4B. CALCULATE REFERENCE BACKGROUND POWER LEVEL Pb. Hmean=sum(sum(Hmag(1:64, 1:M)))/(64*M). IF PbOLD>Hmean THEN Pb=PbOLD−0.1 dB, ELSE Pb=PbOLD+0.1 dB. (This is a delta follower of the background power level).
4C. DETERMINATION OF R1 and R2, constants to be used in characterization. T1=transmit burst length in microseconds. T2=pulse repetition period, in microseconds. We know a priori that elements of Hk(1:64) are attached to 1 mm increments in depth. Then R1=axial resolution in mm=c*T1/2, where c=1.54 mm/microsecond, and R2=2*R1. For example, a 20 cycle transmit burst at 2 MHz carrier frequency has R1=7.2 mm, where R2=14.4 mm.
4D. DETECT EMBOLUS SIGNATURE by examining each column of Hmag(1:64,1:M) and determining longest contiguous segment of data such that each element in the contiguous segment is greater than Pb+XdB (X=3, e.g.). More specifically, let Hk(1:64)=Hmag(1:64,k). Locate longest sequence within Hk, demarcated by starting and ending indices Hk(i1:i2), such that Hk(i)>Pb+X if i1<= i<=i2. The length of this sequence is then determined by fitting the first three points of Hk(i1:i2) with a parabola, and finding the left most point on the abscissa, z1, where the parabola crosses the ordinate of Pb. If the parabola does not intersect the line y=Pb, then z1=i1. Similarly, the last three points of Hk(i1:i2) are fitted with a parabola and z2 is located. If the parabola does not intersect the line y=Pb, then z2=i2. The length of Hk(i1:i2) is z2−z1. IF z2−z1<R1, then no embolus is present. If R1<z2−z1<R2, then a particulate is present. If z2−z1>R2, then a bubble is present.
4E. Pass this information along to P4. If P4 agrees that an embolus is being detected, then attach the characterization information.

Those skilled in the art will appreciate that the invention may be accomplished with circuits other than those particularly depicted and described in connection with FIGS. 9–11. These figures represent just one of many possible implementations of a Doppler ultrasound system in accordance with the invention. Likewise, the invention may be accomplished using process steps other than those particularly depicted and described in connection with FIGS. 12–16.

Those skilled in the art will also understand that each of the circuits whose functions and interconnections are described in connection with FIGS. 9–11 is of a type known in the art. Therefore, one skilled in the art will be readily able to adapt such circuits in the described combination to practice the invention. Particular details of these circuits are not critical to the invention, and a detailed description of the internal circuit operation need not be provided. Similarly, each one of the process steps described in connection with FIGS. 12–16 will be understood by those skilled in the art, and may itself be a sequence of operations that need not be described in detail in order for one skilled in the art to practice the invention.

It will be appreciated that, although specific embodiments of the invention have been described for purposes of illustration, various modifications may be made without deviating from the spirit and scope of the invention. For example, a user interface in accordance with the present invention may be provided by means other than a video display, such as a printer or other visual display device. Those skilled in the art will also appreciate that many of the advantages associated with these circuits and processes described above may be provided by other circuit configurations and processes. Accordingly, the invention is not limited by the particular disclosure above, but instead the scope of the invention is determined by the following claims.

What is claimed is:

1. A visual display device for providing information in connection with Doppler ultrasound monitoring of blood flow, comprising:

a display controller structured to control a first graphical display and a second graphical display, the first graphical display to indicate as a function of time a plurality of locations along an ultrasound beam axis at which blood flow is detected by varying intensity as a function of detected Doppler ultrasound signal amplitude at each of the locations, the second graphical display to indicate velocities of monitored blood flow at a selected location included in the first graphical display.

2. The user interface of claim 1 wherein the plurality of locations is a first plurality and wherein the graphical display indicates a second plurality of locations along the ultrasound beam axis at which blood flow is not detected.

3. The user interface of claim 1 wherein the first graphical display includes first and second colors associated with blood flow in first and second directions, respectively, the first and second colors having intensities varying as a function of detected Doppler ultrasound amplitude.

4. The user interface of claim 1 wherein the first graphical display includes a color region corresponding with the locations at which blood flow is detected.

5. The user interface of claim 1 wherein the first graphical display includes a color region corresponding with the locations at which blood flow is detected, the color having varying intensity as a function of a detected Doppler ultrasound signal amplitude.

6. The user interface of claim 1 wherein the first graphical display includes a color region corresponding with the locations at which blood flow is detected, the color associated with detected blood flow direction and having varying intensity as a function of a detected Doppler ultrasound signal amplitude.

7. The user interface of claim 1 wherein the first graphical display includes a color region corresponding with the locations at which blood flow is detected, the color associated with detected blood flow direction and having varying intensity as a function of detected blood flow velocities and detected Doppler ultrasound signal amplitude.

8. The user interface of claim 1 wherein the second graphical display is a spectrogram indicating the velocities of the monitored blood flow at the selected location as a function of time.

9. The user interface of claim 1 wherein the first and second graphical displays are provided simultaneously.

10. The user interface of claim 1 wherein the display controller further controls the first graphical display to display a location indicator identifying the selected location.

11. The user interface of claim 10 wherein the first graphical display includes a color region corresponding with the locations at which blood flow is detected, the location indicator being a pointer directed towards a position within the color region, and wherein the second graphical display is a spectrogram indicating the velocities of the monitored blood flow at the selected location as a function of time.

12. A graphical display for providing information in connection with Doppler ultrasound monitoring of blood flow, comprising:

a display controller to provide a blood locator display to depict as a function of time a plurality of locations along an ultrasound beam is at which blood flow is detected by varying intensity as a function of detected Doppler ultrasound amplitude at each of the locations, and to further provide a spectrogram to depict detected blood flow velocities as a function of time at a selected one of the plurality of locations.

13. The graphical display of claim 12 wherein the display controller further provides a location indicator identifying the selected location.

14. The graphical display of claim 13 wherein the location indicator is a pointer directed to the selected location depicted in the blood locator display.

15. The graphical display of claim 12 wherein the blood locator display includes a color region corresponding to the depicted locations at which blood flow is detected, the color having varying intensity as a function of a detected Doppler ultrasound signal amplitude.

16. The graphical display of claim 12 wherein the blood locator display includes a color region corresponding to the depicted locations at which blood flow is detected, the color associated with blood flow direction and having varying intensity as a function of a detected Doppler ultrasound signal amplitude.

17. The graphical display of claim 12 wherein the blood locator display includes a color region corresponding to the depicted locations at which blood flow is detected, the color associated with blood flow direction and having varying intensity as a function of a detected blood flow velocities and detected Doppler ultrasound amplitude.

18. The graphical display of claim 12 wherein the blood locator display and the spectrogram are displayed simultaneously.

19. The graphical display of claim 12 wherein the plurality of locations is a first plurality and wherein the graphical display indicates a second plurality of locations along the ultrasound beam axis at which blood flow is not detected.

20. A graphical display for a Doppler ultrasound system to provide information in connection with Doppler ultrasound monitoring of blood flow, comprising:

a display controller;

a blood locator display coupled to the display controller and having a color region to depict as a function of time a plurality of locations along an ultrasound beam axis at which blood flow is detected, the color of the color region having its intensity vary as a function of detected Doppler ultrasound amplitude; and a spectrogram coupled to the display controller to depict detected blood flow velocities as a function of time at a selected one of the plurality of locations.

21. The graphical display of claim 20 wherein the color region has one of first and second colors corresponding with first and second detected blood flow directions.

22. The graphical display of claim of claim 20 wherein the color region has one of first and second colors corresponding with first and second detected blood flow directions, the intensity of the color varying as a function of detected blood flow velocity and Doppler ultrasound signal amplitude.

23. The graphical display of claim 20, further comprising a location indicator identifying the selected location.

24. The graphical display of claim 23 wherein the location indicator is a pointer directed towards a position within the color region corresponding to the selected location.

25. The graphical display of claim 23 wherein the location indicator is a pointer directed towards a position within the colored region corresponding to the selected location, and wherein the colored region has one of first and second colors corresponding with first and second detected blood flow directions, the intensity of the color varying as a function of detected blood flow velocity and Doppler ultrasound signal amplitude.

26. The graphical display of claim 20 wherein the blood locator display and the spectrogram are displayed simultaneously.

27. The graphical display of claim 20 wherein the plurality of locations is a first plurality and wherein the graphical display indicates a second plurality of locations along the ultrasound beam axis at which blood flow is not detected.

28. A Doppler ultrasound system for processing ultrasound signals along an ultrasound beam axis and for displaying information to a user concerning blood flow, comprising:
an ultrasound transducer operable to detect ultrasound signals and responsively produce corresponding electrical signals;
signal processing circuitry coupled with the transducer and operable to receive the electrical signals and determine blood flow characteristics corresponding with the detected ultrasound signals;
a display coupled with the signal processing circuitry and operable to provide aiming graphical information indicating as a function of time a plurality of locations along the beam axis at which blood flow is detected by varying intensity as a function of detected Doppler ultrasound am amplitude at each of the locations, and to further provide spectral graphical information indicating blood flow velocities at a selected one of the locations indicated by the aiming graphical information.

29. The Doppler ultrasound system of claim 28 wherein the aiming graphical information includes a color region corresponding with the locations at which blood flow is detected, the color associated with blood flow direction and having varying intensity as a function of one of detected blood flow velocity and detected Doppler ultrasound signal strength.

30. The Doppler ultrasound system of claim 28 wherein the display provides the aiming and spectral graphical information simultaneously.

31. The Doppler ultrasound system of claim 28, wherein the display further comprises a location indicator identifying the selected location.

32. The Doppler ultrasound system of claim 31 wherein the location indicator is a pointer directed towards a position within the display region corresponding to the selected location.

33. The Doppler ultrasound system claim 28 wherein the plurality of locations is a first plurality and wherein the graphical display indicates a second plurality of locations along the ultrasound beam axis at which blood flow is not detected.

34. In a Doppler ultrasound system for processing ultrasound signals along an ultrasound beam axis, a method of providing information to a user concerning blood flow, comprising:
displaying first graphical information depicting as a function of time blood flow at a plurality of locations along the beam axis by varying intensity as a function of detected Doppler ultrasound amplitude at each of the locations; and
displaying second graphical information depicting blood flow velocities at a selected one of the locations displayed by the first graphical information.

35. The method of claim 34 wherein displaying the first graphical information includes displaying a location indicator directed to the selected location.

36. The method of claim 34 wherein the selected location is determined by the user.

37. The method of claim 34 wherein displaying the first graphical information includes displaying a color region corresponding with locations where blood flow is detected.

38. The method of claim 34 wherein displaying the first graphical information includes displaying color having a varying intensity in correspondence with detected Doppler ultrasound signal amplitude.

39. The method of claim 34 wherein displaying the first graphical information includes displaying one of first and second colors corresponding to blood flow in first and second directions, respectively.

40. The method of claim 34 wherein displaying the first graphical information includes displaying one of first and second colors corresponding to blood flow in first and second directions, respectively, and varying the intensity of the first and second colors in correspondence with detected blood flow velocities and detected Doppler ultrasound amplitude.

41. The method of claim 34 wherein displaying the first graphical information includes displaying one of first and second colors corresponding to blood flow in first and second directions, respectively, and varying the intensity of the first and second colors in correspondence with detected Doppler ultrasound signal amplitude.

42. The method of claim 34 wherein the first and second graphical information are displayed simultaneously.

43. The method of claim 34 wherein the plurality of locations is a first plurality and wherein the graphical display indicates a second plurality of locations along the ultrasound beam axis at which blood flow is not detected.

44. In a Doppler ultrasound system for processing ultrasound signals along an ultrasound beam axis, a method of detecting and characterizing emboli in blood flow, comprising:
determining a first plurality of locations along the beam axis in which blood flows and determining a second plurality of locations along the beam axis in which blood does not flow;
determining the direction in which the blood flows at each of the first locations; and
if a first ultrasound signal having an intensity greater than a threshold intensity is received, then:
determining if the first ultrasound signal corresponds with the first locations;
determining if the first ultrasound signal corresponds with the second locations;
determining if the first ultrasound signal corresponds with the determined direction and velocity of the blood flow;
if the first ultrasound signal does not correspond with the determined direction or velocity of the blood flow, then identifying the first ultrasound signal as a non-embolic signal;
if the first ultrasound signal corresponds with the determined direction or velocity of the blood flow, and if the first ultrasound signal corresponds solely with the first locations, then identifying the first ultrasound signal as an embolic signal of a first type; and
if the first ultrasound signal corresponds with the determined direction and velocity of the blood flow, and if the first ultrasound signal corresponds both with the first and second locations, then identifying the first ultrasound signal as an embolic signal of a second type.

45. The method of claim 44, further comprising selecting one of the first locations, and wherein the first ultrasound signal is a signal corresponding with the selected location.

46. The method of claim 44 wherein determining the first plurality of locations in which blood flows includes displaying graphical information having a color region corresponding to the first locations.

47. The method of claim 44 wherein determining the first plurality of locations in which blood flows includes displaying graphical information having a color region corresponding to the first locations, and wherein determining the direction in which the blood flows at each of the first locations includes selecting one of first and second colors for the color region, the first and second colors corresponding with first and second blood flow directions along the beam axis, respectively.

48. The method of claim 44 wherein determining the first plurality of locations in which blood flows includes displaying graphical information having a color region corresponding to the first locations, and varying the intensity of the color as a function of detected Doppler ultrasound signal intensity, and wherein determining if the first ultrasound signal corresponds with the first locations includes displaying a graphical event signal corresponding with the first ultrasound signal and determining if the graphical event signal is positioned within the color region.

49. The method of claim 44 wherein determining the first plurality of locations in which blood flows includes displaying graphical information having a color region corresponding to the first locations, and varying the intensity of the color as a function of detected Doppler ultrasound signal intensity, and wherein determining if the first ultrasound signal corresponds with the determined direction and velocity of blood flow includes displaying a graphical event signal corresponding with the first ultrasound signal and determining if the graphical event signal is positioned in a predetermined orientation relative to the color region.

50. The method of claim 44 wherein determining if the first ultrasound signal corresponds with the determined direction and velocity of blood flow includes determining if the first ultrasound signal corresponds with a velocity not exceeding a maximum velocity of the blood flow.

51. In a Doppler ultrasound system for processing ultrasound signals along an ultrasound beam axis, a method of locating a selected one of a plurality of blood vessels, comprising:
  determining a plurality of locations along the beam axis in which blood flows;
  displaying first graphical information depicting the locations at which blood flow is detected;
  determining the velocity with which blood flows in each of the locations;
  selecting a first one of the locations;
  displaying second graphical information depicting blood flow velocities at the first location;
  detecting a temporal variation in the first graphical information;
  detecting a temporal variation in the second graphical information; and
  determining whether the detected temporal variations in the first and second graphical information corresponds with the selected blood vessel.

52. The method of claim 51 wherein displaying the first graphical information includes displaying a color region corresponding with the locations at which blood flow is detected.

53. The method of claim 51 wherein displaying the first graphical information includes displaying a color region corresponding with the locations at which blood flow is detected, and varying the intensity of the color as a function of detected Doppler ultrasound signal intensity.

54. The method of claim 51 wherein displaying the first graphical information includes displaying a color region corresponding with the locations at which blood flow is detected, and varying the intensity of the color as a function of the determined blood flow velocities.

55. The method of claim 51 wherein displaying the first graphical information includes displaying a color region corresponding with the locations at which blood flow is detected, and wherein detecting a temporal variation in the first graphical information includes detecting a temporal variation in the size of the color region.

56. The method of claim 51 wherein displaying the first graphical information includes displaying a color region corresponding with the locations at which blood flow is detected, and varying the intensity of the color as a function of the determined blood flow velocities, and wherein detecting a temporal variation in the first graphical information includes detecting a temporal variation in the color intensity of the color region.

57. A computer readable medium whose contents configure a computer system to provide information to a user concerning blood flow detected by processing Doppler ultrasound signals along an ultrasound beam axis, comprising:
  displaying first graphical information depicting as a function of time blood flow at a plurality of locations along the beam axis by varying intensity as a function of detected Doppler ultrasound amplitude at each of the locations; and
  displaying second graphical information depicting blood flow velocities at a selected one of the plurality of locations.

58. The computer readable medium of claim 57 wherein displaying the first graphical information includes displaying a location indicator directed to the selected location.

59. The computer readable medium of claim 57 wherein the selected location is determined by a user of the computer system.

60. The computer readable medium of claim 57 wherein displaying the first graphical information includes displaying a color region corresponding with locations where blood flow is detected.

61. The computer readable medium of claim 57 wherein displaying the first graphical information includes displaying color having a varying intensity in correspondence with detected Doppler ultrasound signal amplitude.

62. The computer readable medium of claim 57 wherein displaying the first graphical information includes displaying one of first and second colors corresponding to blood flow in first and second directions, respectively.

63. The computer readable medium of claim 57 wherein displaying the first graphical information includes displaying one of first and second colors corresponding to blood flow in first and second directions, respectively, and varying the intensity of the first and second colors in correspondence with detected blood flow velocities and detected Doppler ultrasound amplitude.

64. The computer readable medium of claim 57 wherein displaying the first graphical information includes displaying one of first and second colors corresponding to blood flow in first and second directions, respectively, and varying the intensity of the first and second colors in correspondence with detected Doppler ultrasound signal amplitude.

65. The computer readable medium of claim 57 that further configure the computer system to display the first and second graphical information simultaneously.

66. The user interface of claim 57 wherein the plurality of locations is a first plurality and wherein the graphical display indicates a second plurality of locations along the ultrasound beam axis at which blood flow is not detected.

\* \* \* \* \*

UNITED STATES PATENT AND TRADEMARK OFFICE
CERTIFICATE OF CORRECTION

PATENT NO. : 6,196,972 B1
DATED : March 6, 2001
INVENTOR(S) : Mark A. Moehring

It is certified that error appears in the above-identified patent and that said Letters Patent is hereby corrected as shown below:

Column 1,
Line 9, add -- STATEMENT AS TO GOVERNMENT RIGHTS

This invention was made with United States Government support under Grant No. 2 R44 HL 57108 –02 awarded by National Institutes of Health (NIH). The United States Government has certain rights in this invention. --

Column 15,
Line 64, "ultrasound beam is" -- ultrasound beam axis is --

Column 16,
Line 47, "of claim of claim 20" -- of claim 20 --

Column 17,
Line 21, "ultrasound am amplitude" -- ultrasound amplitude --

Signed and Sealed this

Sixteenth Day of October, 2001

Attest:

NICHOLAS P. GODICI
*Attesting Officer*   *Acting Director of the United States Patent and Trademark Office*